United States Patent
Glenn et al.

(10) Patent No.: US 8,871,435 B2
(45) Date of Patent: Oct. 28, 2014

(54) METHODS AND COMPOSITIONS FOR IDENTIFYING AGENTS THAT INHIBIT AN NS4B-MEDIATED NEOPLASTIC CELLULAR PHENOTYPE OF HCV INFECTED CELLS

(75) Inventors: Jeffrey S. Glenn, Palo Alto, CA (US); Shirit Einav, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1001 days.

(21) Appl. No.: 12/143,630

(22) Filed: Jun. 20, 2008

(65) Prior Publication Data

US 2009/0083869 A1      Mar. 26, 2009

Related U.S. Application Data

(60) Provisional application No. 60/946,684, filed on Jun. 27, 2007.

(51) Int. Cl.
| | |
|---|---|
| *C12Q 1/02* | (2006.01) |
| *C12Q 1/18* | (2006.01) |
| *C12Q 1/70* | (2006.01) |
| *C12N 5/00* | (2006.01) |
| *G01N 33/50* | (2006.01) |
| *A61K 49/00* | (2006.01) |

(52) U.S. Cl.
CPC ........ *G01N 33/5011* (2013.01); *A61K 49/0008* (2013.01)
USPC .................. 435/5; 435/29; 435/325

(58) Field of Classification Search
CPC ....................... G01N 33/5011; A61K 49/0008
See application file for complete search history.

(56) References Cited

U.S. PATENT DOCUMENTS

| | | | |
|---|---|---|---|
| 2002/0147160 A1 | 10/2002 | Bhat et al. | |
| 2003/0087873 A1 | 5/2003 | Stuyver et al. | |
| 2006/0199174 A1 | 9/2006 | Glenn et al. | |
| 2007/0269420 A1* | 11/2007 | Chunduru et al. | 424/130.1 |

FOREIGN PATENT DOCUMENTS

| | | | |
|---|---|---|---|
| WO | WO9901582 A1 | | 1/1999 |
| WO | WO 2005032329 A2 * | | 4/2005 |
| WO | WO 2005051318 A2 * | | 6/2005 |

OTHER PUBLICATIONS

Pakula et al. Genetic Analysis of Protein Stability and Function. Annual Reviews of Genetics 1989, vol. 23, pp. 289-310.*

Bartenschlager, R., et al. Replication of hepatitis C virus. Journal of General Virology. 2000, vol. 81, pp. 1631-1648.
Chang, J., et al. Hepatitis C virus core from two different genotypes has an oncogenic potential but is not sufficiet for transforming primary rat embryo fibroblasts in cooperation with the H-ras oncogene. Journal of Virology. 1998, vol. 72, No. 4, pp. 3060-3065.
Einav, S., et al. A nucleotide binding motif in hepatitis C virus (HCV) NS4B mediates NCV RNA replication. Journal of Virology. 2004, vol. 78, No. 20, pp. 11288-11295.
Einav, S., et al. The nucleotide binding motif of hepatitis C virus NS4B can mediate cellular transformation and tumor formation without Ha-ras con-transfection. Hepatology. 2008, vol. 47, pp. 827-835.
Gorbalenya, A., et al. Viral proteins containing the purine NTP-binding sequence pattern. Nucleic Acids Research. 1989, vol. 17, No. 21, pp. 8413-8440.
Hugle, T., et al. The hepatitis C virus nonstructural protein 4B is an integral endoplasmic reticulum membrane protein. Virology. 2001, vol. 284, pp. 70-81.
Mirzayan, C., et al. Genetic analysis of an NTP-binding motif in poliovirus polypeptide 2C. Virology. 1992, vol. 189, pp. 547-555.
Ray, R., et al. Hepatitis C virus core protein cooperates with ras and transforms primary rat embryo fibroblasts to tumorigenic phenotype. Journal of Virology. 1996, vol. 70, No. 7, pp. 4438-4443.
Rodriguez, P., et al. Poliovirus protein 2C has ATPase and GTPase activities. The Journal of Biological Chemistry. 1993, vol. 286, No. 11, pp. 8105-8110.
Florese, R., et al. Inhibition of protein synthesis by the nonstructural proteins NS4A and NS4B of hepatitis C virus. Virus Research. 2002, vol. 90, pp. 119-131.
Park, J., et al. Hepatitis C virus nonstructural protein NS4B transforms NIH3T3 cells in cooperation with the Ha-ras oncogene. Biochemical and Biophysical Research Communications. 2000, vol. 267, pp. 581-587.
Piccininni, S., et al. Modulation of the hepatitis C virus RNA-dependent RNA polymerase activity by the non-structural (NS) 3 helicase and the NS4B membrane protein. The Journal of Biological Chemistry. 2002, vol. 277, No. 47, pp. 45670-45670.

* cited by examiner

*Primary Examiner* — Louise Humphrey
(74) *Attorney, Agent, or Firm* — Paula A. Borden; Bozicevic, Field & Francis LLP

(57) ABSTRACT

Methods and compositions for identifying agents that inhibit a neoplastic cellular phenotype mediated by the NS4B protein nucleotide binding motif (NBM) of hepatitis C virus (HCV) are provided. In general, the methods involve contacting a candidate agent with a mammalian cell expressing an NS4B NBM polypeptide of an HCV virus, wherein expression of the NS4B NBM polypeptide in the absence of candidate agent promotes a neoplastic cellular phenotype, and detecting the presence or absence of an effect of the candidate agent on NS4B-mediated promotion of a neoplastic cellular phenotype. The provided methods and compositions find use in a variety of therapeutic and screening applications.

18 Claims, 16 Drawing Sheets

| G protein | A motif | G | PM 2 | B motif |
|---|---|---|---|---|
| Consensus | GXXXXGK(S/T) | | | DXXG |
| Ras family: | | | | |
| RAS | GXGGVGKS | F | T | DTAG |
| RHO | GDGAXGKT | F | T | DTAG |
| YPT (Rab) | GXXXXGK(S/T) | F/Y | T | DTAG |
| ARF's: | GL DAAGKT | F/Y | T | DVGG |
| EFT: | GHVDHGKT | | T | DCPG |

FIG. 1A

| Virus/Protein | A motif | B motif |
|---|---|---|
| Consensus | GXXXXGK(S/T) | D/E |
| P4 Phage/P4α | GP GGSGKS | D |
| HAV/2C | GKRGGGKS | DD |
| Polio/2C | GS PGTGKS | MDD |
| BPV/NSI | GP ASTGKT | EE |
| CPMV/P58 | GKS R TGKS | DD |
| RHDV/2C | GAP GI GKT | DE |

FIG. 1B

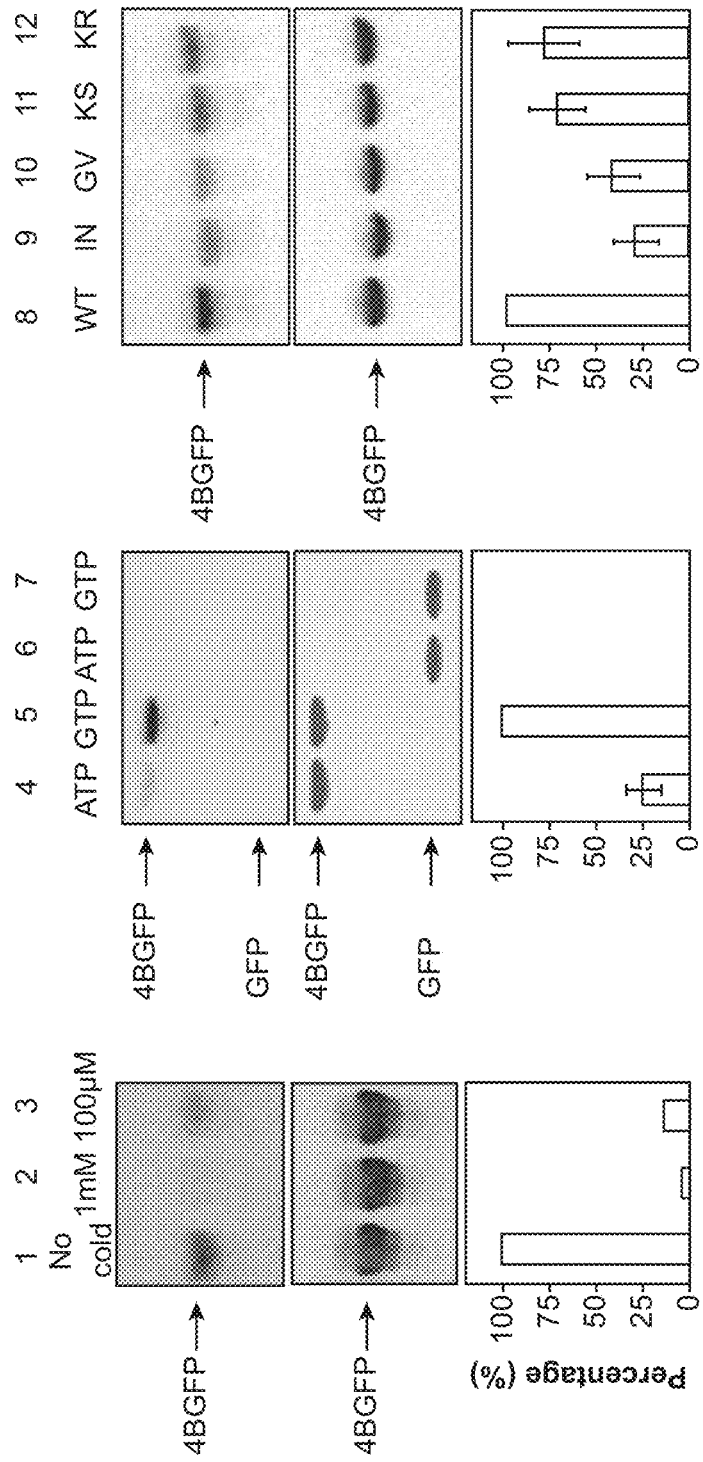

A

| | Contact inhibition | Doubling time | Saturation density | Growth in 1% serum | Soft agar plating efficiency | Soft agar plating efficiency |
|---|---|---|---|---|---|---|
| | | hours | x$10^6$ cells | | # of foci per 5x$10^3$ cells | # of foci per 2x$10^4$ cells |
| pCDNA3.1 | + | 32±2.5 | 0.7±0.1 | - | 0 | 0 |
| Ha-ras | - | 13.7±2.5 | 4.375±0.6 | + | 92±18 | 240±42 |
| NS4B | - | 15±2 | 10.2±3 | + | 153±21 | 467±43 |

Table 1

| Clone name | NS4B | | | | | Neo transfected NIH3T3 | Non transfected NIH3T3 | Ras | | |
|---|---|---|---|---|---|---|---|---|---|---|
| | NS4B1 | NS4B2 | NS4B3 | NS4B4 | NS4B5 | | | Ras1 | Ras2 | Ras3 |
| 2 weeks | 3/5 | 0/5 | 0/5 | 0/5 | 1/5 | 0/3 | 0/13 | 4/5 | 0/4 | 0/3 |
| 5 weeks | 5/5 | 0/5 | 2/5 | 1/5 | 4/5 | 0/3 | 1/13 | 5/5 | 1/4 | 0/3 |

```
            10          20          30          40         50
Con1  ASHLPYIEQG  MQLAEQFKQK  AIGLLQTATK  QAEAAAPVVE  SKWRTLEAFW
K     ----------  ---V------  --L-------  ----------  ------A--P-----

60          70          80          90        100
Con1  AKHMWNFISG  IQYLAGLSTL  PGNPAIASLM  AFTASITSPL  TTQHTLLFNI
K     ----------  ----------  ----------  ----------  ------N---

110         120         130         140        150
Con1  LGGWVAAQLA  PPSAASAFVG  AGIAGAAVGS  IGLGKVLVDI  LAGYGAGVAG
K     ----------  ----------  ----------  ----------  ----------

160         170         180         190        200
Con1  ALVAFKVMSG  EMPSTEDLVN  LLPAILSPGA  LVVGVVCAAI  LRRHVGPGEG
K     -----I----  --V-------  ----------  ----------  ----------

210         220         230         240        250
Con1  AVQWMNRLIA  FASRGNHVSP  THYVPESDAA  ARVTQILSSL  TITQLLKRLH
K     ----------  ----------  ----------  ----------  ----------

260
Con1  QWINEDCSTP  C
K     ----------  --
```

C
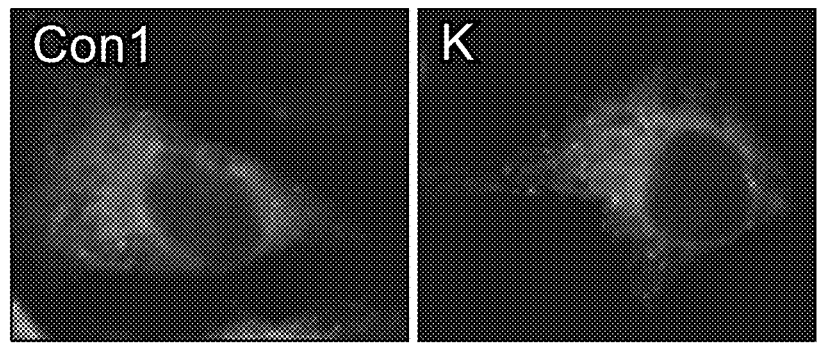
D
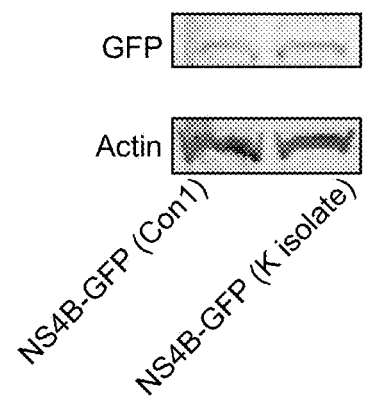
FIG. 10 (Cont.)

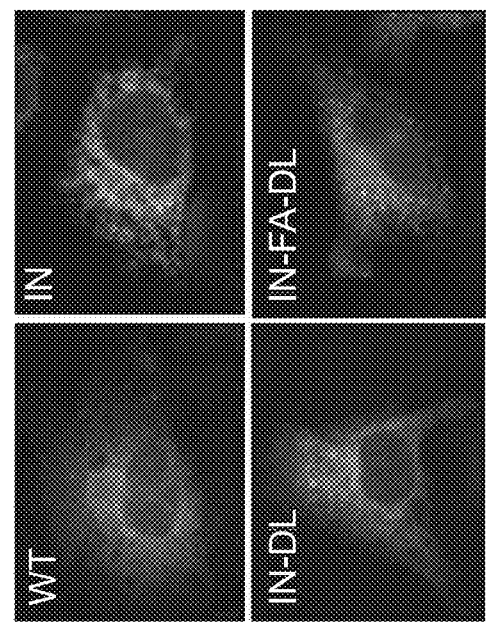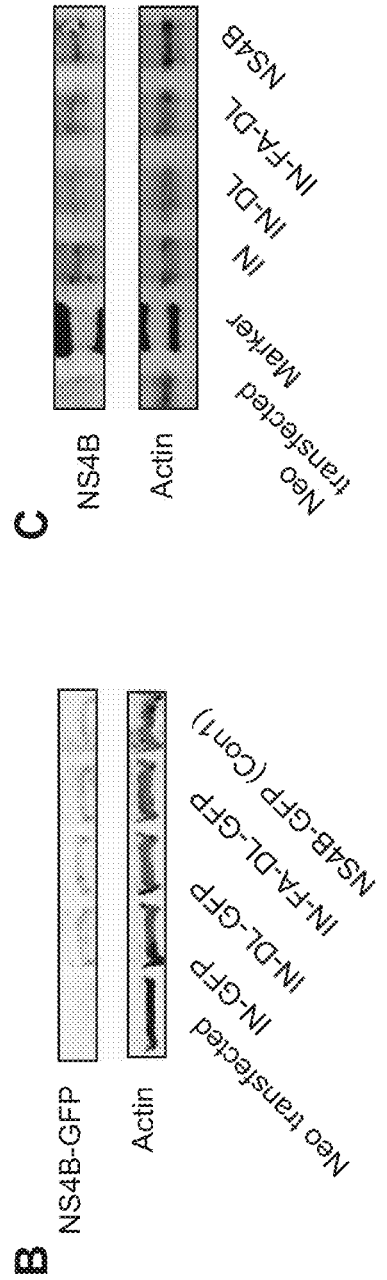
FIG. 12

Table 2

Sequences of the oligonucleotides used in this study

| Primer no. | Primer name[a] | Sequence (5'→3') |
|---|---|---|
| 1 | BamH1-4B-for | CGCGGGATCCGGGATGGCCTCACACCTCCCTTACATCGAACAGGG |
| 2 | EcoR1-4B-rev | CCGGAATTCCTAGCATGGCGTGGAGCAGTCCTCG |
| 3 | I131N-for | GCGGCTGTTGGCAGCAACGGCCTTGGGAAGGTGC |
| 4 | I131N-rev | GCACCTTCCCAAGGCCGTTGCTGCCAACAGCCGC |
| 5 | D228L-for | GTGCCTGAGAGCCTCGCTGCAGCACGTGTCACTCAGATCC |
| 6 | D228L-rev | GTGCCTGAGAGCCTCGCTGCAGCACGTGTCACTCAGATCC |
| 7 | F211A-for | GGATGAACCGGCTGATAGCGGCGCTTCGCGGGGTAACC |
| 8 | F211A-rev | GGTTACCCCGCGAAGCGCCGCTATCAGCCGGTTCATC |
| 9 | MV1-for | CATCGAACAGGGAGTGCAGTCGCCGAAC |
| 10 | MV1-rev | GTTCGGCGAGCTGCACTCCCTGTTCGATG |
| 11 | IL-for | CAAACAGAAGGCACTCGGGTTGCTGCAAACAGC |
| 12 | IL-rev | GCTGTTTGCAGCAACCCGAGTGCCTTCTGTTTG |
| 13 | TA-AP-for | CCAAGTGGGCGGGCCCTCGAACCCTTCTGGGCGAAGC |
| 14 | TA-AP-rev | GCTTCGCCCAGAAGGGTTCGAGGGCCCGCCACTTGG |
| 15 | HN-for | GCTCACCACCCAAAATACCCTCTGTTTAAC |
| 16 | HN-rev | GTTAAACAGAGGGTATTTTGGGTGGTGAGC |
| 17 | VI-MV2-for | GGCCTTTAAGATCATGAGCGGCGAGGTGCCCTCCACCG |
| 18 | VI-MV2-rev | CGGTGGAGGGCACCTCGCCGCTCATGATCTTAAAGGCC |

[a] for, forward primers; rev, reverse primers.

FIG. 13

METHODS AND COMPOSITIONS FOR IDENTIFYING AGENTS THAT INHIBIT AN NS4B-MEDIATED NEOPLASTIC CELLULAR PHENOTYPE OF HCV INFECTED CELLS

CROSS-REFERENCE TO RELATED APPLICATIONS

This application claims the benefit of U.S. Provisional Patent Application No. 60/946,684 (expired), filed Jun. 27, 2007, which is incorporated herein by reference in its entirety.

GOVERNMENT RIGHTS

This invention was made with Government support under Federal Grant No. RO1-DK066793 awarded by the National Institutes of Health. The Government has certain rights in this invention.

BACKGROUND OF THE INVENTION

Hepatitis C virus (HCV) is an example of a Flaviviridae virus and is the principal etiological agent of post-transfusion and community-acquired non-A non-B hepatitis worldwide. It is estimated that over 150 million people worldwide are infected by the virus. A high percentage of carriers become chronically infected with this pathogen and many patients progress to a state of chronic liver disease, so-called chronic hepatitis C. This group is in turn at high risk for serious liver disease such as liver cirrhosis, hepatocellular carcinoma and terminal liver disease leading to death.

HCV is an enveloped positive strand RNA virus. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce structural and non-structural (NS) proteins. In the case of HCV, the generation of mature nonstructural proteins (NS2, NS3, NS4A, NS4B, NS5A, and NS5B) is effected by two viral proteases. The first one is a metalloprotease located in NS2 that cleaves the NS2-NS3 junction in cis; the second one is a serine protease contained within the N-terminal region of NS3 (henceforth referred to as NS3 protease) and mediates all the subsequent cleavages downstream of NS3, both in cis, at the NS3-NS4A cleavage site, and in trans, at the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components.

The mechanism by which HCV establishes viral persistence and causes a high rate of chronic liver disease has not been elucidated. In addition, chronic infection with the hepatitis C virus (HCV) is a major risk factor for the development of hepatocellular carcinoma (HCC). The incidence of HCC and the mortality rate associated with it are increasing dramatically. While chronic inflammation, fibrosis and liver cell proliferation are considered as a major pathogenic mechanism for the development of HCC, there is increasing data to suggest that direct viral effects may play a role as well.

LITERATURE

Literature of interest includes: Hugle et al, 2001 Virology 284:70-81; Gorbalenya and Koonin 1989 Nucleic Acids Res 17:8413-8440; Bartenschlager and Lohmann 2000 Virology 81 Pt 7:1631-1648; Reed and Rice 2000 Current Topics in Microbiology and Immunology 242:55-84; Mirzayan and Wimmer 1992 Virology 189:547-555; Rodriguez and Carrasco 1993 J. Biol Chem 268:8105-8110; and Piccininni 2002 J. Biol Chem 277:45670-45679; Ray et al 1996 Virol 70:4438-43; Park et al, 2000 Biochemical and Biophysical Research Communications 267:581-587; Florese et al, 2002 Virus Res. December; 90(1-2):119-31; Chang et al. J Virol 72:3060-5; Gimenez-Barcons et al. J Interferon Cytokine Res 25:152-64; Ray et al. J Virol 70:4438-43; and published patent applications US20030087873, US20020147160, US20060199174 and WO99/01582.

SUMMARY OF THE INVENTION

The disclosure provides methods and compositions for identifying agents that modulate a neoplastic cellular phenotype mediated by the NS4B protein nucleotide binding motif (NBM) of hepatitis C virus (HCV). In general, the methods involve contacting a candidate agent with a mammalian cell expressing an NS4B NBM polypeptide of an HCV virus, wherein expression of the NS4B NBM polypeptide in the absence of candidate agent promotes a neoplastic cellular phenotype, and detecting the presence or absence of an effect of said candidate agent on NS4B-mediated promotion of a neoplastic cellular phenotype. The disclosed methods and compositions find use in a variety of therapeutic and screening applications.

BRIEF DESCRIPTION OF THE DRAWINGS

FIGS. 1A and 1B show conserved sequence elements in nucleotide binding motif (NBM)-containing proteins. One conserved element of the NBM is the so-called "A-motif." Other conserved elements that may participate in nucleotide binding ("G," "PM2," "B-motif") are also indicated. FIG. 1A shows consensus sequences for the NBM from some representative family members of the G-protein superfamily of GTP-binding proteins. FIG. 1B shows consensus sequences of the NBM for selected viruses. X=any amino acid. GXXXXGK(S/T): SEQ ID NO:1; GXGGVGKS: SEQ ID NO: 2; GDGAXGKT: SEQ ID NO: 3; GLDAAGKT: SEQ ID NO: 4; GHVDHGKT: SEQ ID NO: 5; DTAG: SEQ ID NO: 6; DVGG: SEQ ID NO: 7; DCPG: SEQ ID NO: 8; GPGGSGKS: SEQ ID NO: 9; GKRGGGKS: SEQ ID NO: 10; GSPGT-GKS: SEQ ID NO: 11; GPASTGKT: SEQ ID NO: 12; GKSRTGKS: SEQ ID NO: 13; GAPGIGKT: SEQ ID NO: 14.

FIGS. 3A-3C display results showing that the NS4B NBM is specific for GTP and sensitive to genetic mutation. FIGS. 3A, 3B and 3C are each composed of an autoradiograph (top), a western blot analysis with an anti-GFP antibody (middle) and a graph quantifying nucleotide binding relative to wild type control (bottom). (3A) Binding of labeled GTP is progressively decreased in the presence of increasing concentrations of cold competitor nucleotide. Huh-7 cells were transfected with a plasmid encoding NS4B-GFP. Membrane preparations were incubated with 10 µM labeled GTP compound in the absence (lane 1) or presence of 1 mM (lane 2) or 100 µM (lane 3) competing cold GTPγS, followed by immunoprecipitation as in FIG. 2A above. (3B) NS4B-GFP binds ATP significantly less efficiently than GTP. Membrane preparations prepared from Huh-7 cells transfected with plasmids encoding NS4B-GFP (lanes 4 and 5) or GFP (lanes 6 and 7) were incubated with equal concentrations of labeled ATP (lanes 4 and 6) or GTP (lanes 5 and 7), followed by immunoprecipitation as in FIG. 2A. (3C) Mutations within the NBM impair GTP binding. Huh-7 cells were transfected with plasmids encoding wild type NS4B-GFP (lane 8) or NS4B-GFP with one of the following NBM mutations: Ile131Asn mutation ("IN") (lane 9), Gly129Val mutation ("GV") (lane 10), Lys135Ser mutation ("KS") (lane 11) or Lys135Arg ("KR") (lane 12). As above, membrane fractions were incubated with labeled GTP followed by immunoprecipitation. Experiments were repeated between two to four times. When present, any detectable binding of GTP to the 5A-GFP negative control protein was used for background subtraction purposes. Representative gels are shown. Mean values are plotted in the graphs and error bars represent SE.

FIG. 9 shows Table 1 which indicates that NS4B transfected NIH3T3 cells are tumorigenic in nude mice. NS4B, Ha-ras, and neomycin stable transfectants as well as non-transfected NIH3T3 cells were injected subcutaneously into the flanks of Balb/c nude mice. Tumors were measured bi-weekly and cross sectional area was calculated. A tumor was defined as a growth with a cross sectional area larger than 150 mm$^2$. Data at 2 weeks and 5 weeks after inoculation are documented. Data are the number of mice with tumors/total number of mice inoculated.

FIG. 12 shows that mutations within NS4B's NBM are not associated with obvious changes in intracellular distribution pattern (Panel A) or expression level in transient (Panel B) or stable transfectants (Panel C). Panel A: Huh-7 cells plated on coverslips were transfected with plasmids encoding wild-type NS4B-GFP (WT) or NS4B-GFP with one of the following NBM mutations: I131N (IN), I131N-D228L (IN-DL) and I131N-F211A-D228L (IN-FA-DL). 48 hours posttransfection the cells were fixed and imaged by a fluorescence microscope. Note that all of these proteins display the same reticular membrane localization pattern with distinct foci located in the cytoplasm that is characteristic of wild-type NS4B. Panel B: Cell lysates were prepared from cells transfected with wild-type or NBM mutant forms of NS4B-GFP and subjected to western blot analysis with rabbit anti-GFP (Molecular probes) and mouse anti-actin (Sigma) antibodies. Panel C: Representative colonies were isolated from plates transfected with wild-type or NBM mutant forms of NS4B, and passaged in the presence of G418. Cell lysates prepared from these stable clones were subjected to western blot analyses using mouse anti-NS4B (Virostat) and mouse anti-actin (Sigma) antibodies.

FIG. 13 shows Table 2 which describes the sequences of oligonucleotide primers used in connection with the experiments described herein.

```
BamH1-4B-for:
                                      SEQ ID NO:21
CGCGGATCCGGGATGGCCTCACACCTCCCTTACATCGAACAGGG:.
EcoR1-4B-rev:
                                      SEQ ID NO:22
CCGGAATTCCTAGCATGGCGTGGAGCAGTCCTCG:.
I131N-for:
                                      SEQ ID NO: 23
GCGGCTGTTGGCAGCAACGGCCTTGGGAAGGTGC:.
I131N-rev:
                                      SEQ ID NO: 24
GCACCTTCCCAAGGCCGTTGCTGCCAACAGCCGC:.
D228L-for:
                                      SEQ ID NO: 25
GTGCCTGAGAGCCTCGCTGCAGCACGTGTCACTCAGATCC:.
D228L-rev:
                                      SEQ ID NO: 26
GTGCCTGAGAGCCTCGCTGCAGCACGTGTCACTCAGATCC:.
F211A-for:
                                      SEQ ID NO: 27
GGATGAACCGGCTGATAGCGGCCGCTTCGCGGGGTAACC:.
F211A-rev:
                                      SEQ ID NO: 28
GGTTACCCCGCGAAGCGGCCGCTATCAGCCGGTTCATC:.
```

```
-continued
MV1-for:
                                      SEQ ID NO: 29
CATCGAACAGGGAGTGCAGCTCGCCGAAC:.
MV1-rev:
                                      SEQ ID NO: 30
GTTCGGCGAGCTGCACTCCCTGTTCGATG:.
IL-for:
                                      SEQ ID NO: 31
CAAACAGAAGGCACTCGGGTTGCTGCAAACAGC:.
IL-rev:
                                      SEQ ID NO: 32
GCTGTTTGCAGCAACCCGAGTGCCTTCTGTTTG:.
TA-AP-for:
                                      SEQ ID NO: 33
CCAAGTGGCGGGCCCTCGAACCCTTCTGGGCGAAGC:.
TA-AP-rev:
                                      SEQ ID NO: 34
GCTTCGCCCAGAAGGGTTCGAGGGCCCGCCACTTGG:.
HN-for:
                                      SEQ ID NO: 35
GCTCACCACCCAAAATACCCTCCTGTTTAAC:.
HN-rev:
                                      SEQ ID NO: 36
GTTAAACAGGAGGGTATTTTGGGTGGTGAGC:.
VI-MV2-for:
                                      SEQ ID NO: 37
GGCCTTTAAGATCATGAGCGGCGAGGTGCCCTCCACCG:.
VI-MV2-rev:
                                      SEQ ID NO: 38
CGGTGGAGGGCACCTCGCCGCTCATGATCTTAAAGGCC:.
```

Figure 14:
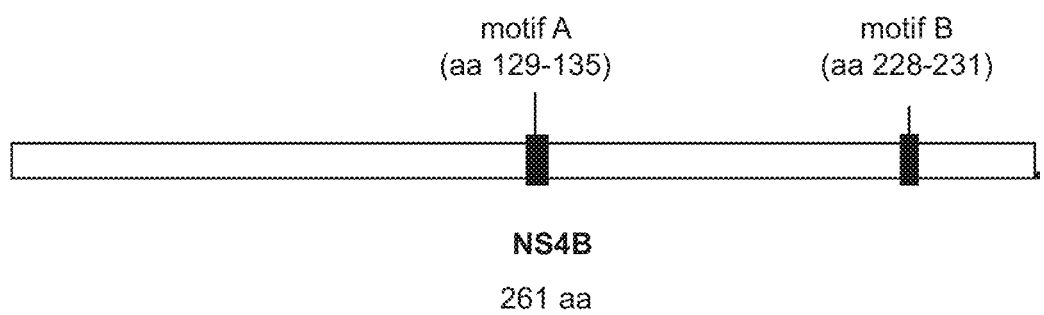

FIG. 14 is a schematic representation of an HCV NS4B protein showing NBM motifs A and B.

Figure 15:
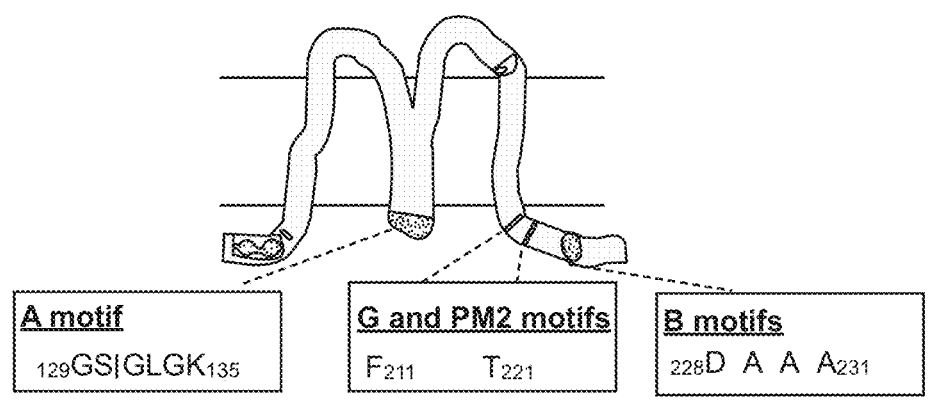

FIG. 15 An analysis of the amino acid sequence of NS4B protein suggests the topology illustrated in FIG. 15 relative to the ER lumen wherein the N- and C- termini are cytosolically oriented. The A (GSIGLGK; SEQ ID NO:18), G, PM2 and B (DAAA; SEQ ID NO:17) motifs of NS4B NBM are indicated.

DEFINITIONS

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an NS4B polypeptide" includes a plurality of such polypeptides and reference to "the NS4B nucleotide binding motif" includes reference to one or more NS4B nucleotide binding motifs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A "nucleotide binding motif" or "NBM" as used herein refers to a region of a viral NS4B polypeptide that binds a nucleotide triphosphate (NTP), which NTP can be GTP, ATP, TTP, or CTP, and usually is at least GTP.

A "nucleotide binding NS4B protein" or "NS4B protein" is any viral NS4B protein, or functional equivalent thereof (e.g., proteins that are encoded by other viruses and are equivalent to NS4B, but not named NS4B), that contains a nucleotide binding motif, binds a nucleotide, and binds RNA in the presence of a nucleotide. NS4B proteins are typically characterized by an N-terminal amphipathic helix, at least two transmembrane domains, and an NBM, where the NBM facilitates nucleotide binding. NS4B proteins may be identified using a number of methods, e.g., by pairwise sequence alignment between the HCV NS4B protein and the proteins encoded by other viruses. The NS4B polypeptide may also itself be contained within a larger polypeptide such as one encoding a replication-competent form of a viral polyprotein.

A "variant" of a polypeptide (e.g., an NS4B polypeptide or an NS4B nucleotide binding motif of a polypeptide) is defined as a polypeptide that is altered by one or more amino acid residues. Such alterations include amino acid substitutions, deletions or insertions, or a combination thereof. Variants of NS4B, particularly those that have conservative amino acid substitutions, usually retain their basic structural features and biological activity. Variants of an NS4B nucleotide binding motif may retain a nucleotide binding activity, allow HCV virus replication and promote a neoplastic cellular phenotype. NS4B variants may alternatively have decreased nucleotide binding activity (e.g., a decreased binding affinity or avidity relative to a wildtype NS4B of, for example, the same viral origin), may have constitutive nucleotide binding activity, or may have enhanced nucleotide binding activity (e.g., an increased binding affinity or avidity relative to a wildtype NS4B of, for example, the same viral origin). A variant NS4B NBM may have decreased ability to promote a neoplastic cellular phenotype.

Guidance in determining which and how many amino acid residues may be substituted, inserted or deleted (e.g., without abolishing activity) may be found by comparing the sequence of a polypeptide to the sequence of a polypeptide with a related structure and function e.g., between sequences from HCV strains or genotypes. Assays for HCV are readily available and straightforward, and can be readily applied to determine empirically which and how many amino acid residues may be substituted, inserted or deleted.

A "substitution" results from the replacement of one or more amino acids or nucleotides by different amino acids or nucleotides, respectively as compared to an amino acid sequence or nucleotide sequence of a polypeptide. If a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: gly, ala; val, ile, leu; asp, glu; asn, gln; ser, thr; lys, arg; and phe, tyr. It is understood that NS4B NBM polypeptides may have conservative amino acid substitutions which have substantially no affect on HCV viral replication or promotion of a neoplastic cellular phenotype. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide or polynucleotide sequence, a deletion can involve deletion of about 2, about 5, about 10, up to about 20, up to about 30 or up to about 50 or more amino acids. An NS4B NBM polypeptide may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition of one or more amino acid residues within an amino acid sequence of a polypeptide, while "addition" can be an insertion or refer to amino acid residues added at the N- or C-termini. In the context of a polypeptide or polynucleotide sequence, an insertion or addition may be of up to about 10, up to about 20, up to about 30 or up to about 50 or more amino acids. A NS4B NBM polypeptide may contain more than one insertion.

A "biologically active" NS4B polypeptide refers to a polypeptide having structural and biochemical functions of a naturally occurring NS4B protein.

A "neoplastic cellular phenotype" refers to a cellular phenotype characterized by, for example, abnormal cell growth, abnormal cellular proliferation, loss of density dependent growth inhibition, continued cellular proliferation despite serum depletion, anchorage-independent growth potential, ability to promote tumor growth and/or development in an immuno-compromised non-human animal model, or any appropriate indicator of cellular transformation.

"Non-native", "non-endogenous", and "heterologous", in the context of a polypeptide, are used interchangeably herein to refer to a polypeptide having an amino acid sequence or, in the context of an expression system or a viral particle, present in an environment different to that found in nature.

"Exogenous" in the context of a nucleic acid or polypeptide is used to refer to a nucleic acid or polypeptide that has been introduced into a host cell. "Exogenous" nucleic acids and polypeptides can be native or non-native to the host cell, where an exogenous, native nucleic acid or polypeptide provides for elevated levels of the encoded gene product or polypeptide in the recombinant host cell relative to that found in the host cell prior to introduction of the exogenous molecule.

The term "Ha-ras oncogene" refers to a Ha-ras gene which when expressed in a mammalian cell promotes a neoplastic cellular phenotype of the mammalian cell. The Ha-ras oncogene may be endogenous or exogenous to the mammalian cell and the ability to promote a neoplastic cellular phenotype of the mammalian cell may result from activating mutations in the DNA sequence encoding the Ha-ras gene or by virtue of overexpression of the Ha-ras gene and/or increased signaling by an upstream receptor.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in-vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Operably linked" refers to an arrangement of elements wherein the components so described are configured so as to perform their usual function. Thus, a given polypeptide that is operably linked to a HCV NS4B nucleotide binding motif binds nucleotides. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Ma dison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address :www.ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., infra; *DNA Cloning, supra; Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

A first polynucleotide is "derived from" a second polynucleotide if it has the same or substantially the same nucleotide sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of modified NS4B polypeptide-encoding nucleic acids that can provide for enhanced or desirable effects in the subject (e.g., reduction of pathogen load, increase in CD4 count, reduction of disease symptoms, etc.).

"Subject", "host" and "patient" are used interchangeably herein, to refer to an animal, human or non-human, susceptible to or having an infection by an intracellular pathogen and amenable to therapy according to the methods of the invention. Generally, the subject is a mammalian subject. Exemplary subjects include, but are not necessarily limited to subjects susceptible to HCV infection, particularly with development of hepatocellular carcinoma (HCC).

DETAILED DESCRIPTION OF THE INVENTION

The disclosure provides methods and compositions for screening agents for activity in modulating a neoplastic cellular phenotype mediated by the NS4B nucleotide binding motif (NBM) of hepatitis C virus (HCV). In general, the methods involve contacting a candidate agent with a mammalian cell expressing an NS4B NBM polypeptide of an HCV virus, wherein expression of the NS4B NBM polypeptide in the absence of candidate agent promotes a neoplastic cellular phenotype, and detecting the presence or absence of an effect of said candidate agent on the NS4B-mediated neoplastic cellular phenotype.

The disclosure also provides methods for identifying an agent that modulates a neoplastic cellular phenotype of cells infected with hepatitis C virus (HCV). In general the methods involve contacting an NS4B nucleotide binding motif (NBM) polypeptide with a candidate agent; determining an effect of the candidate agent on a nucleotide binding activity, a nucleotide hydrolyzing activity, or a nucleotide-dependent RNA binding activity of said polypeptide; and assessing the effect of said candidate agent on a neoplastic cellular phenotype of a mammalian cell expressing an NS4B NBM polypeptide.

Compositions related to the above methods are also disclosed. Generally, these compositions comprise cells comprising a polynucleotide encoding an NS4B polypeptide, which when expressed promote a neoplastic cellular phenotype; and a culture medium suitable for detecting a neoplastic cellular phenotype of the cells. The disclosed methods and compositions find use in a variety of applications.

The role of the nucleotide binding motif (NBM) of hepatitis C virus (HCV) NS4B polypeptide in promoting a neoplastic cellular phenotype can be exploited in assays designed to identify agents capable of modulating a neoplastic cellular phenotype.

In one embodiment, methods and compositions for screening agents for activity in modulating a neoplastic cellular phenotype mediated by an NS4B nucleotide binding motif (NBM) polypeptide of a virus are provided, with HCV viruses being of particular interest. Such agents can be applied to the treatment of conditions characterized by a neoplastic cellular phenotype (e.g. to inhibit the cellular proliferation characteristic of hepatocellular carcinoma (HCC)). In general, the methods involve contacting a candidate agent with a mammalian cell expressing an NS4B NBM polypeptide of an HCV virus, wherein expression of the NS4B NBM polypeptide in the absence of candidate agent promotes a neoplastic cellular phenotype, and detecting the presence or absence of an effect of said candidate agent on the neoplastic cellular phenotype.

In another embodiment, methods for identifying agents that modulate a neoplastic cellular phenotype of cells infected with hepatitis C virus (HCV) are disclosed. In general these methods involve contacting an NS4B nucleotide binding motif (NBM) polypeptide with a candidate agent; determining an effect of the candidate agent on a nucleotide binding activity, a nucleotide hydrolyzing activity, or a nucleotide-dependent RNA binding activity of said polypeptide; and assessing the effect of said candidate agent on a neoplastic cellular phenotype of a mammalian cell expressing an NS4B NBM polypeptide.

Also disclosed, is a composition comprising a recombinant mammalian cell exhibiting a neoplastic cellular phenotype which includes anchorage-independent growth when cultured in soft agar, wherein said recombinant mammalian cell comprises an expression construct encoding an NS4B nucleotide binding motif (NBM) polypeptide, and wherein expression of the NS4B NBM promotes the neoplastic cellular phenotype of the recombinant mammalian cell, with the proviso that the recombinant mammalian cell does not express an exogenous Ha-ras oncogene.

The mammalian cell of the disclosed composition may be an NIH3T3 cell or other cell capable of exhibiting a neoplastic cellular phenotype in connection with the expression of NS4B NBM.

The disclosure further provides an NS4B polypeptide having a modified nucleotide binding motif, e.g., a nucleotide binding motif that is impaired in nucleotide binding, and/or the ability to promote a neoplastic cellular phenotype, and a polynucleotide encoding this polypeptide. The disclosure also provides modified viral genomes encoding a modified NBM. The disclosed methods and compositions find use in a variety of applications.

The disclosed HCV may be of any genotype (genotype 1, 2, 3, 4, 5, 6, and the like), as well as subtypes of an HCV genotype (e.g., 1a, 1b, 2a, 2b, 3a, etc.)). Because currently HCV genotype 1 is normally the most difficult to treat, and thus most commonly associated with chronic infection, HCV genotype 1 and genotype 1 subtypes are of particular interest.

In further describing the invention in greater detail than provided in the Summary and as informed by the Background and Definitions provided above, the compositions for use in the disclosed methods are described first, followed by a discussion of methods for screening agents for activity in modulating a neoplastic cellular phenotype and methods for identifying agents that modulate a neoplastic cellular phenotype of cells infected with an HCV virus, a review of representative applications in which the disclosed methods find use, and disclosed kits provided for practicing the disclosed methods.

NS4B NBM Polypeptides

An "NS4B NBM polypeptide" is a polypeptide that contains an NS4B NBM and that, when expressed in a mammalian cell in the absence of an exogenous Ha-ras oncogene gene product, promotes a neoplastic cellular phenotype. Thus, an NS4B NBM polypeptide encompasses, for example, a polypeptide that contains an NBM from an HCV NS4B protein (e.g., a naturally-occurring NS4B protein), a fusion protein containing an NBM-containing fragment of an NS4B polypeptide or full-length NS4B polypeptide, operably linked to a fusion partner, a polypeptide that comprises a variant NS4B NBM (including fusion proteins thereof) that retains activity in promoting a neoplastic cellular phenotype, or the like, provided that the NS4B NBM polypeptide is capable of promoting a neoplastic cellular phenotype in a mammalian cell in the absence of an exogenous Ha-ras oncogene gene product. Such polypeptides find use in, for example, screening assays for agents with activity in inhibiting a neoplastic cellular phenotype.

The NS4B NBM polypeptide referenced above may be a naturally-occurring NS4B protein or a variant thereof, or in other embodiments, a non-naturally occurring NS4B protein or a variant thereof, provided that the protein or variant thereof is capable of promoting a neoplastic cellular phenotype in a mammalian cell in the absence of an exogenous Ha-ras oncogene gene product.

In certain embodiments the fusion partner may be a reporter protein, e.g., a light emitting reporter such as a fluorescent or luminescent polypeptide (for example GFP or luciferase), may contain sequences from another nucleotide-binding polypeptide (e.g., a G-protein), or may contain sequence from any other polypeptide. In particular embodiments, an NS4B NBM polypeptide is a fusion protein between an NS4B NBM and a partner such as GST, polyhistidine, or avidin. These fusions are convenient for assay formats using glutathione, nickel, or biotin coupled to solid supports (using beads or a microtiter plate well, etc.).

The NS4B NBM polypeptides referenced above contain either an NS4B NBM or a variant NS4B NBM. An "NS4B NBM" is generally defined as having a sequence conforming to an NS4B NBM consensus amino acid sequence comprising: an A motif consensus sequence of G-S/G-I/V-G-L/I-G-K/R: SEQ ID NO. 16, a G motif consensus F (Phenylalanine) residue, a PM2 motif consensus T (Threonine) residue, and a B motif consensus sequence of DAAA: SEQ ID NO:17. In certain embodiments, the NS4B NBM has an A motif of the sequence GSIGLGK: (SEQ ID NO: 18), a G motif with an F (Phenylalanine) residue, a PM2 motif with a T (Threonine) residue, and a B motif with the sequence DAAA: (SEQ ID NO: 17).

A polypeptide comprising a variant NS4B NBM, and having activity in promoting a neoplastic cellular phenotype, generally has one or more amino acid substitutions relative to the NBM consensus sequences set out above, but retains the ability to promote a neoplastic cellular phenotype when expressed in a mammalian cell in the absence of an exogenous Ha-ras oncogene gene product. For example, substitution of an "N" in the (I/V) position of the A motif results in a decrease in the promotion of a neoplastic cellular phenotype but does not abolish the ability of the NS4B NBM polypeptide comprising a variant NS4B NBM to promote a neoplastic cellular phenotype. A double mutation including the substitution of an "N" in the (I/V) position of the A motif and an "L" in the D position of the B motif results in a further decrease in the promotion of a neoplastic cellular phenotype but also does not abolish the ability of the NS4B NBM polypeptide comprising a variant NS4B NBM to promote a neoplastic cellular phenotype.

Those of ordinary skill in the art will be able to readily identify NS4B NBM polypeptides having the ability to promote a neoplastic cellular phenotype, by performing assays similar to those described in the Examples below.

NS4B NBM polypeptides that retain nucleotide-binding activity usually have a sequence conforming to the NS4B NBM consensus sequence: G-S/G-I/V-G-L/I-G-K/R (SEQ ID NO:16) or, in other embodiments G-S/G-I-G-L-G-K/R (SEQ ID NO:39), and in addition, may have NS4B NBM motifs G, PM2 and B, spaced from the consensus sequence at an appropriate distance, as discussed in Dever et al., (Proc Natl Acad Sci U S A. 1987 84:1814-8) although their precise spacing distance is not as important as their relationship to each other in the polypeptide tertiary structure.

Nucleic Acids Encoding NS4B NBM Polypeptides

Since the genetic code and recombinant techniques for manipulating nucleic acid are known, and the amino acid sequences of NS4B NBM polypeptides are described above, the design and production of nucleic acids encoding a NS4B NBM polypeptide is well within the skill of an artisan. In certain embodiments, standard recombinant DNA technology (Ausubel, et al, *Short Protocols in Molecular Biology,* 3rd ed., Wiley & Sons, 1995; Sambrook, et al., *Molecular Cloning: A Laboratory Manual*, Second Edition, (1989) Cold Spring Harbor, N.Y.) methods are used. For example, naturally occurring NS4B NBM polypeptide coding sequences may be isolated from a library of nucleic acids using any one or a combination of a variety of recombinant methods that do not need to be described herein. Subsequent substitution, deletion, and/or addition of nucleotides in the nucleic acid sequence encoding a protein may also be done using standard recombinant DNA techniques.

For example, site directed mutagenesis and subcloning may be used to introduce/delete/substitute nucleic acid residues in a polynucleotide encoding a NS4B NBM polypeptide. In other embodiments, PCR may be used. Nucleic acids encoding a NS4B NBM polypeptide may also be made by chemical synthesis entirely from oligonucleotides (e.g., Cello et al., Science (2002) 297:1016-8).

In certain embodiments, the codons of the nucleic acids encoding an NS4B NBM polypeptide are optimized for expression in cells of a particular species, particularly a mammalian, e.g., human or mouse, species.

Vectors (also referred to as "constructs") comprising a nucleic acid encoding a NS4B NBM polypeptide are also disclosed. In many embodiments, a nucleic acid sequence encoding a NS4B NBM polypeptide may be expressed in a host after the sequence has been operably linked to an expression control sequence, including, e.g. a promoter. The NS4B NBM polypeptide encoding nucleic acids are typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology,* 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used. In certain embodiments, however, the disclosed nucleic acids are contained in the genome of HCV, where the genome has been genetically modified such that it contains a non-naturally occurring NS4B polypeptide-encoding sequence.

A variety of expression vectors are available to those in the art for purposes of producing a polypeptide of interest in a cell. One suitable vector is pCMV, which used in certain embodiments. This vector is publicly available from the American Type Culture Collection (ATCC) and was deposited on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The nucleic acids encoding a NS4B NBM polypeptide usually contain a single open reading frame, however, in certain embodiments, since the host cell for expression of the polypeptide of interest may be a eukaryotic cell, e.g., a mammalian cell, such as a human cell, the open reading frame may be interrupted by introns. Nucleic acids encoding a NS4B NBM polypeptide are typically part of a transcriptional unit which may contain, in addition to the disclosed nucleic acids 3' and 5' untranslated regions (UTRs) which may direct RNA stability, translational efficiency, etc. The disclosed nucleic acids may also be part of an expression cassette which contains, in addition to the disclosed nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the disclosed vectors as a selectable marker is chosen primarily as a matter of convenience. Known selectable marker genes include: the thimydine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, NS4B NBM polypeptides may be fusion proteins. Methods for making fusions between two or more nucleic acids encoding a fusion protein, are well within the skill of one of skill in the art and will not be described any further.

Nucleic acids encoding NS4B NBM polypeptides may also contain restriction sites, multiple cloning sites, primer binding sites, ligatable ends, recombination sites etc., usually in order to facilitate the construction of a nucleic acid encoding a polypeptide of interest.

In certain embodiments, a nucleic acid of interest may be a modified viral (e.g., HCV) genome, or model thereof, that encodes an NS4B polypeptide having altered nucleotide binding activity and/or altered activity in promoting a neoplastic cellular phenotype, as described above. In these embodiments, the nucleic acid, either RNA or DNA, may be part of a virus particle. In certain embodiments, viral nucleic acids encoding a wild-type NS4B NBM are replaced by nucleic acids encoding an NS4B NBM with modified nucleotide binding activity and/or altered activity in promoting a neoplastic cellular phenotype.

Host Cells

The invention further provides host cells, including isolated in-vitro host cells (e.g., for construct production and/or use in screening assays) and in-vivo host cells of a non-human animal, that comprise a disclosed nucleic acid and/or polypeptide.

*E. coli* is a prokaryotic host useful for cloning nucleic acid sequences in connection with the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* or *Pichia* are preferred hosts, with suitable vectors having expression control sequences, such as promoters, including the 3-phosphoglycerate kinase promoter or those of other glycolytic enzyme genes, and an origin of replication, termination sequences and the like as desired.

In addition to microorganisms, mammalian tissue cell culture may also be used to express and produce NS4B NBM polypeptides in connection with the present invention (see, Winnacker, "From Genes to Clones," VCH Publishers, New York, N.Y. (1987). Suitable mammalian cells include CHO cell lines, various COS cell lines, HeLa cells, and myeloma cell lines, etc.

Modified polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Polypeptides can also be synthesized in the laboratory. Polypeptides that are subsets of the complete sequences of the disclosed proteins may be used to identify and investigate parts of the protein important for function.

Other embodiments of particular interest include host cells useful in the screening methods disclosed herein. In certain embodiments, the host cell is a mammalian cell which exhibits a neoplastic cellular phenotype when an NSB4 NBM polypeptide is expressed therein. In certain further embodiments, a mammalian cell which exhibits a neoplastic cellular phenotype when an NSB4 NBM polypeptide is expressed therein is an NIH3T3 cell, or a primary cell susceptible to cellular transformation (e.g., primary embryo fibroblast, e.g., a primary rat embryo fibroblast). In some embodiments, a mammalian cell which exhibits a neoplastic cellular phenotype when an NSB4 NBM polypeptide is expressed therein is a cell which does not express an exogenous Ha-ras oncogene.

The disclosure also contemplates host cells suitable for use in the assays disclosed herein. For example, where it may be desirable to provide for HCV replication, the host cell is a mammalian (e.g.) human cell that may be infected with HCV (including models thereof). In certain embodiments the human cell is a CHOP cell, a huh7 cell or a H9C2 cell, B-cell lines including B-cell lymphoma cells, and the cell is chosen because it is susceptible to infection by HCV or can support the replication of HCV or HCV replicons. The latter include a wide variety of cells (including but not limited to primary human, mouse, or rat liver cells, or cell lines originally derived from primary cells such as HeLa, Hepa-6, MDCK, etc.) where each cell type has its own set of preferred adaptive mutations.

Animal Models

In addition, the disclosure contemplates use of animal models of viral infection, particularly HCV infection. Mouse models, in particular the mouse models for HCV, described in PCT publication WO01/67854, may be used. The disclosure further contemplates the use of non-human animal models of oncogenesis. In certain embodiments these non-human animal models comprise a recombinant mammalian cell, wherein said recombinant mammalian cell comprises a polynucleotide encoding an exogenous NS4B nucleotide binding motif (NBM) polypeptide, wherein expression of the exogenous NS4B NBM polypeptide promotes oncogenesis in the non-human animal. In certain further embodiments, a non-human animal model comprising a recombinant mammalian cell, wherein said recombinant mammalian cell comprises a polynucleotide encoding an exogenous NS4B nucleotide binding motif (NBM) polypeptide, and wherein expression of the exogenous NS4B NBM polypeptide promotes oncogenesis in the non-human animal, is an immuno-compromised non-human animal, e.g. a nude mouse, scid (severe combined immune deficiency) mouse, or Rag1 mouse.

Screening Assays

The disclosure provides methods of screening an agent for activity in modulating a neoplastic cellular phenotype. In general, the methods involve contacting a candidate agent with a mammalian cell expressing an NS4B NBM polypeptide, wherein expression of the NS4B NBM polypeptide in the absence of candidate agent promotes a neoplastic cellular phenotype, and detecting the presence or absence of an effect of said candidate agent on the NS4B NBM polypeptide-mediated neoplastic cellular phenotype. In one embodiment, the "mammalian cell" is an NIH3T3 cell which does not express an exogenous Ha-ras oncogene, and the modulation of a neoplastic cellular phenotype is an inhibition of a neoplastic cellular phenotype.

The disclosure also provides methods for identifying an agent that modulates a neoplastic cellular phenotype of cells infected with hepatitis C virus (HCV). In general the methods involve contacting a NS4B nucleotide binding motif (NBM) polypeptide with a candidate agent; determining an effect of the candidate agent on a nucleotide binding activity, a nucleotide hydrolyzing activity, or a nucleotide-dependent RNA binding activity of said polypeptide; and assessing the effect of said candidate agent on a neoplastic cellular phenotype of a mammalian cell expressing an NS4B NBM polypeptide. In one embodiment, the effect of said candidate agent on a neoplastic cellular phenotype is an inhibitory effect on a neoplastic cellular phenotype.

In many embodiments, a candidate agent that inhibits a nucleotide binding activity of the polypeptide is an agent which inhibits a neoplastic cellular phenotype of a cell in which the polypeptide is expressed. What is meant by "inhibits a nucleotide binding activity" is reducing an activity related to nucleotide binding, such as, for example, the affinity of the polypeptide to a nucleotide, the specificity of the polypeptide to a nucleotide, or, in certain embodiments, a conformation change in the polypeptide that is induced by nucleotide binding or the ability of the polypeptide to catalyze a reaction of said nucleotide (e.g., hydrolysis, etc), where the nucleotide can be dGTP, dATP, dTTP or dCTP, including analogs and/or variants thereof, including ribonucleotides, etc., and polymers thereof.

In general, agents identified using the disclosed screening assays will inhibit an activity (i.e., a nucleotide binding activity, a nucleotide hydrolyzing activity, a nucleotide-dependent RNA binding activity, or a neoplastic cellular phenotype promoting activity) of an NS4B NBM polypeptide by more than about 20%, more than about 40%, more than about 60%, more than about 80%, more than about 90%, or more than about 95%, or more than about 98%, usually up to about 100%, as compared to the same activity of a NS4B NBM polypeptide in the absence of a candidate agent.

The portion of the protein employed in such screening may be free in solution, affixed to an abiotic or biotic substrate (e.g. borne on a cell surface), or located intracellularly.

Prior to or following cell-based assays to assess the effect of an agent upon a neoplastic cellular phenotype, assays may be performed in a cell free system, using NS4B NBM polypeptide that is in solution or immobilized in a solid support to identify agents that bind the NBM. In other embodiments, NBM binding can be assessed by using a cell containing an NS4B NBM polypeptide within the cell or on its surface.

Assays for nucleotide binding are generally very well known in the art (for example, as described in Feig, Mol Endocrinol. 1987 February; 1(2):127-36; Sigal, Anticancer Drug Des. 1987 October; 2(2):107-15; Colman, Adv Exp Med Biol. 1990; 281:257-63; Ali, J Pharmacol Toxicol Methods. 1994 December; 32(4):187-96; and Farr, Natl. Acad. Sci. USA. 1990 Jul. 1; 87 (13): 5041-5045), and generally involve producing a nucleotide binding polypeptide bound to a solid support, incubating the polypeptide with a labeled nucleotide, washing the solid support, and determining if the nucleotide is associated with the solid support. Other assays may involve assays for nucleotide hydrolysis, which are also well known in the art (e.g., Wilkes, Biochem Biophys Res Commun. 2002 Aug. 16; 296(2):388-94; Krumins, Methods Enzymol. 2002; 344:673-85; and Tisdale, Mol Biol Cell. 1999 June; 10(6): 1837-49).

Assays for RNA binding are also well known in the art, and may be adapted for use in the disclosed methods. In many embodiments, a polypeptide disclosed herein is contacted with a nucleotide (e.g., G, A, T or C) and candidate agent in the presence of RNA, and RNA binding to the polypeptide is evaluated. Exemplary assays for evaluating RNA binding are well known in the art (see, e.g., Blair et al, RNA 1998 4:215-225; Gallinari et al, J Virol. 1998 72:6758-69; Cheng et al, J Virol. 1999 73:7044-9). An RNA binding assay may employ any RNA, although an RNA derived from the genome of a virus containing an nucleotide-binding NS4B protein (e.g., an HCV genome or any NS4B-binding fragment thereof) may be used.

A variety of different test compounds may be screened using the above methods. Test compounds encompass numerous chemical classes, though typically they are organic molecules, preferably small organic compounds having a molecular weight of more than 50 and less than about 2,500 daltons. Test compounds comprise functional groups necessary for structural interaction with proteins, particularly hydrogen bonding, and typically include at least an amine, carbonyl, hydroxyl or carboxyl group, preferably at least two of the functional chemical groups. The test compounds often comprise cyclical carbon or heterocyclic structures and/or aromatic or polyaromatic structures substituted with one or more of the above functional groups. Test compounds are also found among biomolecules including peptides, saccharides, fatty acids, steroids, purines, pyrimidines, derivatives, structural analogs or combinations thereof.

Test compounds may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In particular, candidate agents that are nucleotide variants, e.g., variants of nucleotides, nucleosides, ribonucleotides, etc., such as dGTP, dATP, dTTP and dCTP or variants thereof are of particular use. For example, non-hydrolysable nucleotides, GTPγS, GppNHp, GMPPCP, 5'-adenylylimidodiphosphate, guanosine 5'-3-O-(thio)triphosphate, 5'-O-(thio)triphosphate and adenosine 5'-(βγ-imino)triphosphate, Gpp(NH)p, etc may be used. In some variants, the ribose moiety can be replaced with carbocyclics, smaller and larger rings, conformationally constrained rings, and acyclics. Conformational constraints such as fused cyclopropane and cyclopentane rings in place of ribose can also be built into the ribose rings of nucleoside and nucleotide ligands. Phosphate analogs may also be used. Further examples of nucleotide variants may be found in Jacobson et al., (Nucleic Acids. 2001 20:333-41) and Plunkett et al., (Cancer Chemother Biol Response Modif. 2001; 19:21-45).

In particular embodiments, agents that bind to the NS4B NBM but not NBMs from host (e.g. human) proteins are desirable because they may inhibit GTP binding activity of the NS4B, but do not inhibit GTP binding activity of human proteins. Such agents, e.g., monoclonal antibodies, phage display peptides, etc, may be identified using a number of approaches. In one embodiment, monoclonal antibodies that specifically bind a NS4B NBM are produced and tested against a number of host protein NBMs, or a protein having a consensus host NBM. In another embodiment, a phage display library is screened for phage that bind to a NS4B NBM but not host NBMs, or a consensus thereof.

An agent, which may be identified using the above assays, may be assayed in a variety of cellular and animal models, for example, models of NS4B mediated hepatocellular carcinoma (HCC).

In-Vitro Cell Based Assays

In some embodiments of the invention, an agent's ability to modulate a neoplastic cellular phenotype is determined by means of in-vitro cell based assays.

Focus Formation Assay

Generally, an appropriate cell line, which does not express an exogenous Ha-ras oncogene, such as NIH3T3, is transfected with a vector which encodes an NS4B nucleotide binding motif (NBM) polypeptide. After a period of growth under appropriate conditions colonies larger than a predetermined size (e.g., which may be selected as a colony size that is formed in the presence of a neoplastic agent) are counted. The colonies are then analyzed microscopically in order to determine whether a modulation of a neoplastic cellular phenotype has occurred.

In test samples, cells expressing an NS4B NBM polypeptide are treated with a candidate agent prior to colony count and analysis. Where treated cells exhibit a modulation of a neoplastic cellular phenotype as compared with untreated cells expressing an NS4B NBM polypeptide there is an indication that the candidate agent is one which has activity in modulating a neoplastic cellular phenotype.

In certain embodiments, treated cells which exhibit a modulation of a neoplastic cellular phenotype exhibit density-dependent growth inhibition as compared with untreated control cells expressing an NS4B NBM polypeptide. In other embodiments, treated cells exhibit an inhibition in cellular proliferation as compared with untreated control cells expressing an NS4B NBM polypeptide. Standard procedures for carrying out focus formation assays are described in Clark et al. Methods in Enzymology 255:395-412 (1995).

Assays for Growth Rate, Saturation Density, and Serum Dependence

In order to analyze growth rate, saturation density and serum dependence, standard methods such as those disclosed in Clark et al. Methods in Enzymology 255:395-412 (1995) may be used. Generally, an appropriate cell line which does not express an exogenous Ha-ras oncogene, such as NIH3T3, is transfected with a vector which encodes a NS4B nucleotide binding motif (NBM) polypeptide. In one embodiment, cells are seeded at an appropriate density in growth medium and incubated at an appropriate temperature. Cells are then rinsed, trypsinized and counted daily for an appropriate period of time. Growth rates are then determined from the slope of the logarithmic curve during exponential growth. In another embodiment, saturation densities are determined, and in yet another embodiment, serum dependence is determined.

In test samples, cells expressing an NS4B NBM polypeptide are treated with a candidate agent prior to the determination of growth rate, saturation density, or serum dependence. Where treated cells exhibit a modulation of a neoplastic cellular phenotype as compared with untreated cells expressing an NS4B NBM polypeptide there is an indication that the candidate agent is one which has activity in modulating a neoplastic cellular phenotype.

In certain embodiments, treated cells which exhibit a modulation of a neoplastic cellular phenotype exhibit decreased growth rate, decreased saturation density, or serum dependence as compared with untreated control cells expressing an NS4B NBM polypeptide.

Anchorage-Independent Growth Potential

An agent's ability to modulate a neoplastic cellular phenotype can be assessed by determining the anchorage-independent growth potential of cells expressing an NS4B NBM polypeptide in the presence or absence of a candidate agent. Anchorage-independent growth potential may be determined using soft agar assays. Generally, cells expressing an NS4B NBM polypeptide, but not an exogenous Ha-ras oncogene, are suspended in a 0.25% agar mixture and overlayed onto 0.75% agar in cell culture dishes. Cells are fed with growth medium at appropriate intervals. After an appropriate incubation period, colony morphology is assessed microscopically and the number of colonies is counted. Where treated cells exhibit a modulation of a neoplastic cellular phenotype as compared with untreated cells expressing an NS4B NBM polypeptide there is an indication that the candidate agent is one which has activity in modulating a neoplastic cellular phenotype.

In certain embodiments, treated cells which exhibit a modulation of a neoplastic cellular phenotype exhibit decreased anchorage independent growth potential as compared with untreated control cells expressing an NS4B NBM polypeptide. The use of soft agar assays to determine anchorage-independent growth potential are described generally in Clark et al. Methods in Enzymology 255:395-412 (1995).

In-Vivo Assays

In certain embodiments, the disclosed assays include for example, administering candidate agent to a non-human animal model. An agent's ability to modulate a neoplastic cellular phenotype can be assessed by monitoring tumor growth and/or development in non-human animals comprising a recombinant mammalian cell, wherein said recombinant mammalian cell comprises a polynucleotide encoding an exogenous NS4B nucleotide binding motif (NBM) polypeptide, wherein expression of the exogenous NS4B NBM polypeptide promotes tumor growth and/or development in the non-human animal.

The non-human animal of the above model may be treated with a candidate agent and monitored for tumor growth and/or development. Tumor growth and/or development in these animals may be compared with animals of the above model which are not treated with a candidate agent. Where treated animals exhibit a modulation of a neoplastic cellular phenotype as compared with untreated animals there is an indication that the candidate agent is one which has activity in modulating a neoplastic cellular phenotype.

In further embodiments, treated animals which exhibit a modulation of a neoplastic cellular phenotype exhibit decreased tumor growth and/or development as compared with untreated control animals.

In certain embodiments, a non-human animal model suitable for use in the above in-vivo assay is an immuno-compromised non-human animal, e.g. a nude mouse, scid (severe combined immune deficiency) mouse, or Rag1 mouse High-Throughput Assays The disclosure contemplates that many of the assays disclosed herein may be adapted for use in high-throughput screening. For example, assays for focus formation, growth rate, saturation density, serum-growth dependence, and anchorage-independent growth potential may be performed in a multiple well plate format. In other embodiments, automated or semi-automated robotic systems may be used to perform the steps of the respective assays.

For example, the disclosure contemplates the use of an array comprising a plurality of discrete locations, wherein at least two of said discrete locations comprise a recombinant mammalian cell comprising an expression construct encoding an NS4B nucleotide binding motif (NBM) polypeptide with the proviso that the recombinant mammalian cell does not express an exogenous Ha-ras oncogene; and different candidate anti-oncogenic agents in said at least two of said discrete locations. In certain embodiments the recombinant mammalian cell is an NIH3T3 cell.

The disclosure also contemplates the use of various reporters of cellular proliferation, which include reporters of cellular metabolism, such as agents or indicators used in calorimetric assays and radio-labeling assays. These reporters find use in the above arrays as well as other contemplated embodiments. The MTT Cell Proliferation Assay available from ATCC is an example of a suitable cellular proliferation assay which may be performed in a high throughput manner. In this assay, the yellow tetrazolium MTT (3-(4,5-dimethylthiazolyl-2)-2,5-diphenyltetrazolium bromide) is reduced by metabolically active cells, in part by the action of dehydrogenase enzymes, to generate reducing equivalents such as NADH and NADPH. The resulting intracellular purple formazan can be solubilized and quantified by spectrophotometric means. The XTT Cell Proliferation Kit available from PromoKine provides another example of a colorimetric cellular proliferation assay. The XTT Cell Proliferation Assay is a colorimetric assay system which measures the reduction of a tetrazolium component (XTT) into soluble formazan product by the mitochondria of viable cells. The samples are read using an ELISA plate reader at a wavelength of 450 nm. The amount of color produced is directly proportional to the number of viable cells. The ALAMAR BLUE™ dye available from US Biological provides another means of measuring cellular proliferation. Proliferation measurements may be made either spectrophotometrically by monitoring the absorption of ALAMAR BLUE™ supplemented cell culture media at two wavelengths. Alternatively, proliferation measurements with ALAMAR BLUE™ may be made fluorometrically. Radio-labeling assay techniques for measuring cellular proliferation are also available, e.g., 3H-Thymidine incorporation assays.

Kits

Also provided are kits for practicing the disclosed methods. The disclosed kits at least include one or more of: a recombinant NS4B NBM polypeptide or a nucleic acid encoding the same; a recombinant NS4B NBM polypeptide that has reduced nucleotide binding activity as compared to a native NS4B, or a nucleic acid encoding the same; or virus particles containing any of the disclosed compositions. Other optional components of the kit include: adjuvant, carrier, syringes, other anti-viral drugs, reporters of cellular proliferation (such as agents for use in colorimetric assays and radio-labeling assays), etc. Any nucleic acids in the kit may also have restrictions sites, multiple cloning sites, primer sites, etc to facilitate their ligation to other plasmids. The various components of the kit may be present in separate containers or certain compatible components may be precombined into a single container, as desired. In many embodiments, kits with unit doses of the active agent, e.g. in oral or injectable doses, are provided.

In addition to above-mentioned components, the disclosed kits typically further include instructions for using the components of the kit to practice the disclosed methods. The instructions for practicing the disclosed methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Materials and Methods

Plasmids. Standard recombinant DNA technology was used to construct and purify all plasmids. All regions that were amplified by PCR were analyzed by automated DNA sequencing. Plasmid DNAs were prepared from large-scale bacterial cultures and purified by a Maxiprep kit (Marligen Biosciences). Restriction enzymes were purchased from New England Bio Labs (Massachusetts).

The plasmid Bart79I is described in Elazar et al. J Virol 2003 77(10), 6055-6061. Briefly, it was made by PCR mutagenesis of HCVrep1bBartMan/AvaII such that nucleotide 5336 was changed from a G to T resulting in a change in NS5A codon 1179 from serine to isoleucine. This mutation results in a dramatic increase in replication efficiency of the HCV subgenomic replicon.

Additional materials and methods are described in the following examples.

Example 1

NS4B Contains a Nucleotide Binding Motif

Inspection of the NS4B primary sequence revealed the presence of a nucleotide binding motif (NBM) within the middle of NS4B. This motif consists of a set of conserved amino acids found in both the GTP-binding members of the G-protein family, as well as in the superfamily of viral proteins with nucleotide-binding domains. The most highly-conserved elements within these nucleotide-binding domains are the so-called A motif and B motif (FIGS. 1A and 1B).

Example 2

NS4B Binds GTP

The properties associated with the wild type and mutated versions of NS4B's NBM were determined. A plasmid was constructed, termed NS4B-GFP, which encodes a NS4B protein with a C-terminal, in frame green fluorescent protein (GFP) tag. The latter allows for visualization in live cells and provides a convenient epitope outside of any future field of mutagenesis within NS4B. Importantly, GFP fusions to NS4B have been previously reported to have no difference in intracellular localization patterns from those described for wild type NS4B.

To demonstrate that NS4B can bind GTP, GTP-binding experiments using Huh-7 cells infected with a T7RNAP-expressing vaccinia virus and transfected with plasmids encoding NS4B-GFP, GFP, or mock transfected, were performed. Membrane preparations were prepared and aliquots incubated with $^{32}$P-labeled GTP-γ-4-azidoanilide (a UV-photoactivatable non-hydrolyzable GTP analog). Following a brief pulse of UV-irradiation to activate covalent attachment of any bound GTP, pelleted membranes were washed and subjected to immunoprecipitation with a rabbit anti-GFP antibody, SDS-PAGE, transfer to nitrocellulose, autoradiography and western blot.

Figures 2A, 2B:
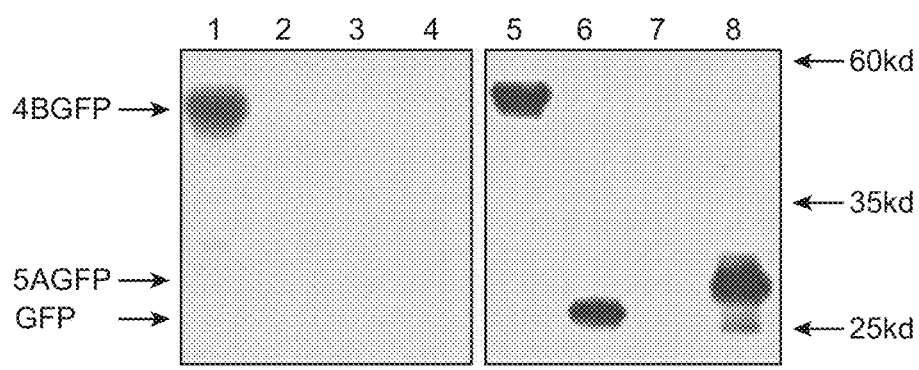
FIGS. 2A and 2B, displaying an autoradiograph and western blot respectively, show that HCV NS4B binds GTP. Membrane preparations from Huh-7 cells transfected with plasmids encoding NS4B-GFP (lanes 1 and 5), GFP (lanes 2 and 6), mock transfected (lanes 3 and 7) or transfected with 5A-GFP (lanes 4 and 8) were incubated with $^{32}$P-labeled photoactivatable GTP. Following one minute of UV-irradiation to activate covalent attachment of any bound GTP, samples were washed and subjected to immunoprecipitation with a rabbit anti-GFP antibody, SDS-PAGE, and autoradiography (2A). Aliquots of the immunoprecipitates were also analyzed by western blot probed with a mouse anti-GFP antibody followed by chemiluminescence detection (2B). Molecular weight markers (in kDa) are indicated on the right.

As shown in FIG. 2A, NS4B-GFP, but not GFP, was specifically labeled with GTP (FIG. 2A, lanes 1 vs. 2). Western analysis with an antibody to GFP of the immunoprecipitates revealed comparable expression levels of the two proteins (FIG. 2B, lanes 5 vs. 6). To provide another measure of the specificity of the observed labeling, assays were performed with plasmid 5A-GFP, which encodes for the first 31 amino acids of HCV NS5A fused in frame to the N-terminus of GFP. The resulting fusion protein thus contains, like NS4B, a potent membrane-targeting N-terminal amphipathic helix yet does not include a known nucleotide binding element. Essentially no GTP labeling of 5A-GFP was observed (FIG. 2A, lane 4) in spite of a larger amount of expressed protein (FIG. 2B, lanes 8 vs. 5). Labeling of 5A-GFP detectable only after extensive film exposure was used for background subtraction purposes in subsequent quantitative analyses. This demonstrates that NS4B has GTP-binding activity. In addition, these results indicate that such binding activity is preserved when NS4B is expressed in the form of a fusion protein.

The specificity of NS4B's GTP binding was further evaluated by performing binding experiments in the presence of excess unlabeled ligand. Membrane aliquots of Huh-7 cells expressing NS4B-GFP were incubated with $^{32}$P-labeled GTP analog as described above, except that cold GTPγS was added to the incubation mixture. As shown in FIG. 3A, binding of labeled GTP was progressively decreased in the presence of increasing concentrations of the cold competitor nucleotide (FIG. 3A, top panel, lane 1 vs. lanes 2 and 3).

Binding assays were performed using Huh-7 cells expressing NS4B-GFP as in FIG. 2. Membrane aliquots were incubated with equal concentrations of $^{32}$P-labeled ATP-γ-4-azidoanilide or GTP-γ-4-azidoanilide analog followed by immunoprecipitation. As shown in FIG. 3B, although NS4B can bind ATP, this appears to be significantly less efficient than GTP binding (FIG. 3B, top panel, lane 4 vs. 5). Again, no labeling of the control GFP was detected with either ATP or GTP (FIG. 3B, top panel, lanes 6 and 7).

Example 3

Mutation of NS4B's NBM Impairs GTP Binding

Figure 4:
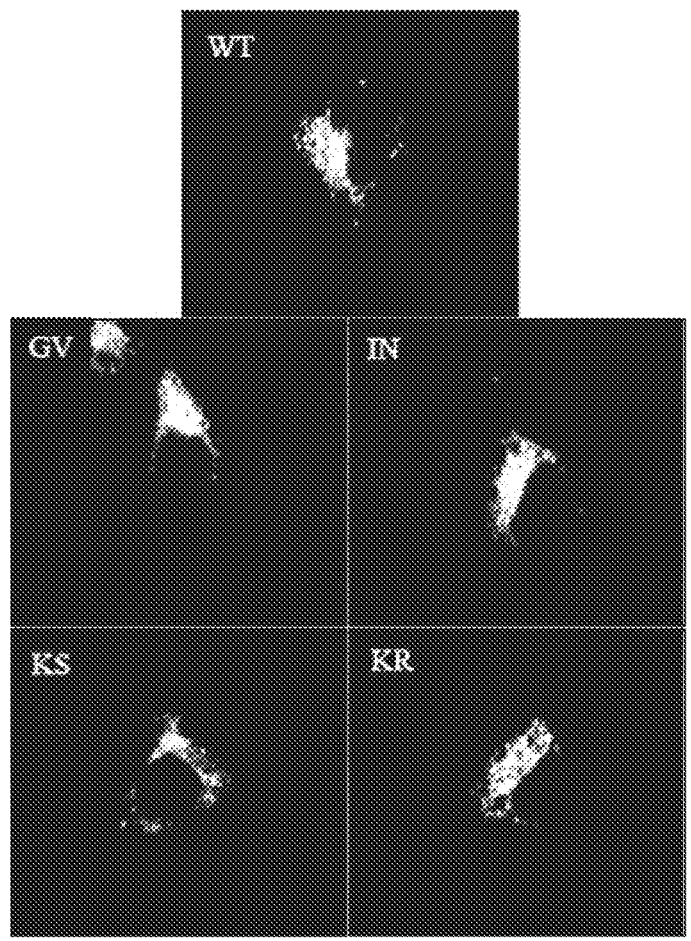
FIG. 4 is five panels of fluorescence images showing that mutations within NS4B's NBM are not associated with obvious changes in protein expression level or intracellular distribution pattern. Huh-7 cells plated on coverslips were transfected with plasmids encoding wild type NS4B-GFP (upper panel), or NS4B-GFP with one of the following NBM mutations: Gly129Val mutation ("GV") (left middle panel), Ile131Asn mutation ("IN") (right middle panel), Lys135Ser mutation ("KS") (left lower panel) or Lys135Arg ("KR") (right lower panel). Eighteen hours post transfection the cells were fixed and imaged by fluorescence microscope. Note that all of these proteins display the same reticular membrane localization pattern with distinct foci located in the cytoplasm that is characteristic of wild type NS4B.

Mutations within the NS4B NBM can impair GTP binding. Four mutants each harboring a single amino acid mutation within the NS4B NBM were utilized. Ile131Asn (or "IN") has a single amino acid change in the second position of the A motif of the NS4B NBM, a position that has been shown to be critical for NBM function in other proteins. The Lys135Ser ("KS") and Lys135Arg ("KR") mutants both have a single amino acid change at position 135. The Gly129Val ("GV") is a single amino acid mutation at the highly conserved first position of the NBM A-motif consensus sequence. These mutations were introduced into NS4B-GFP and GTP binding assays were performed. As shown in the top panel of FIG. 3C, the GV and the IN NBM mutant proteins exhibited a two to three fold reduction in GTP binding on average compared to that of the wild type NS4B-GFP protein (lanes 10 and 9 vs. 8). In contrast, the KS and KR NBM mutants reduced GTP binding activity to a lesser degree (lanes 11 and 12 vs. 8). This was not simply the result of an obvious gross effect of the mutations on folding, as the apparent intracellular expression levels and distribution patterns of mutant and wild type proteins appeared identical by fluorescence microscopy (FIG. 4). Moreover, western analysis with an anti-GFP antibody of the immunoprecipitates again revealed comparable levels of expression of these proteins (FIG. 3C).

Example 4

NS4B has GTPase Activity which is Mediated by the NBM

Figure 5:
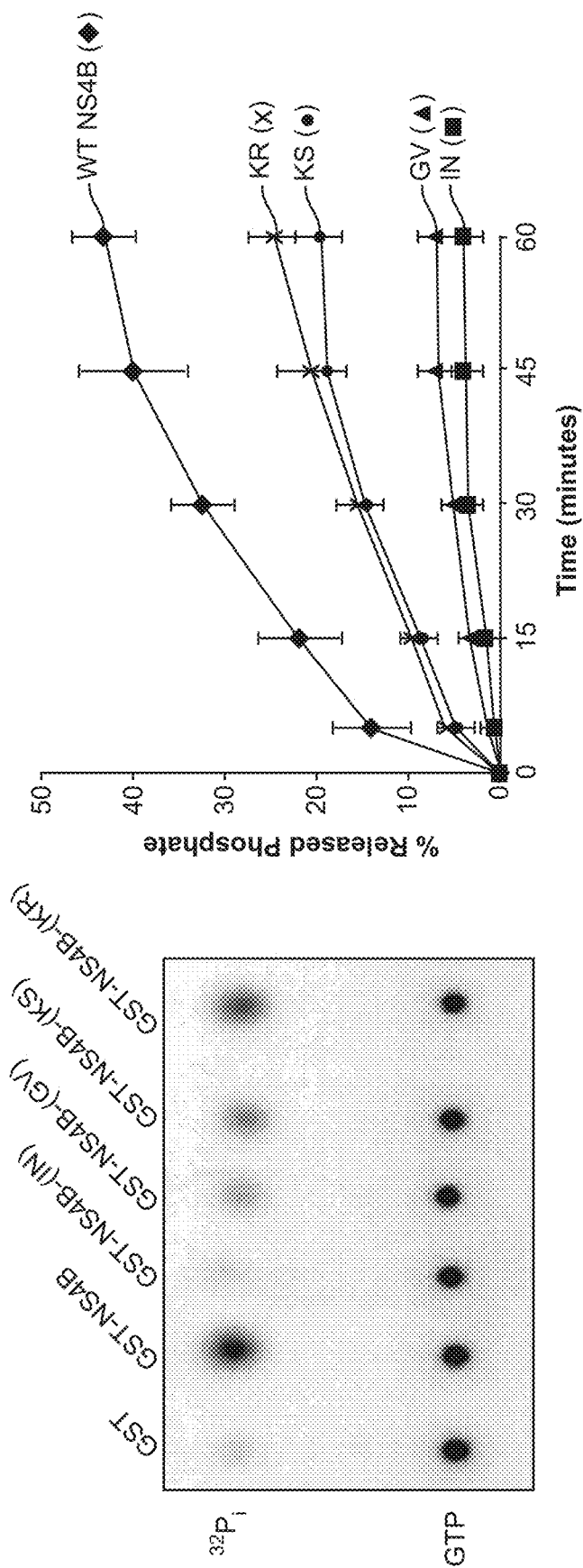
FIGS. 5A and 5B show that NS4B has GTPase activity which is mediated by an NBM. Equal amounts of purified GST, GST-NS4B, and the NBM mutants GST-NS4B(GV), GST-NS4B(IN), GST-NS4B(KS), and GST-NS4B(KR) were incubated with [γ$^{32}$P]GTP. Aliquots were collected every 15 minutes and subjected to thin-layer chromatography (TLC) to allow separation of hydrolyzed $^{32}$Pi from GTP followed by autoradiography and phosphorimager analysis. (5A) A representative TLC plate. Locations of GTP and $^{32}$Pi standards are indicated on the left. (5B) GTPase activity of wild type NS4B (♦), GV (▲), IN (■), KS (●) and KR (x) mutants is plotted as a function of time. When present, any detectable hydrolysis of GTP in the GST control was used for background subtraction purposes. Each data point represents the average of at least four independent determinations. The error bars represent standard deviation.

The NS4B NBM mediates GTP hydrolysis. The wild type NS4B and the four NBM mutants were fused in frame with N-terminal Glutathione-S Transferase (GST) tags and assayed. The resultant fusion proteins, termed GST-NS4B, GST-NS4B-(IN), GST-NS4B-(GV), GST-NS4B-(KS) and GST-NS4B-(KR) were expressed in E. coli BL21 and purified with glutathione beads. The purified proteins were then tested for their ability to hydrolyze GTP by a standard GTPase assay wherein release of phosphate from [$\gamma^{32}$P]GTP was monitored by quantitative thin-layer chromatography, essentially as previously described. Not only does NS4B have GTPase activity, but the latter is sensitive to disruption of the NBM (FIG. 5A and FIG. 5B). Indeed, the targeted mutations could either partially (KS, KR) or nearly completely (GV, IN) abolish GTPase activity.

Example 5

NS4B Transforms NIH 3T3 Cells Independently of Co-Transfected Exogenous Ha-ras

To test whether the con1 isolate of genotype 1b NS4B (Blight et al, 2000 Science 290:1972-4, Lohmann et al, 1999 Science 42 285:110-113) is able to transform NIH3T3 cells when co-expressed with the activated Ha-ras gene, a plasmid termed pcDNA3.1-NS4B was constructed which encodes the con1 NS4B sequence. For this, a PCR fragment of the NS4B gene amplified from the Bart79I plasmid with primers containing BamH1 and EcoR1 restriction sites (primers 1 and 2; FIG. 13 (Table 2) was digested with BamH1 and EcoR1 and ligated into the corresponding site in pcDNA3.1 (Invitrogen). The plasmid pEJ6.6 (Shih et al, 1982 Cell 29:161-9) encoding the Ha-ras gene was also utilized. These plasmids were then used in a standard transfection assay (Bernstein et al, 1985 Proc. of the Natl. Acad. of Sci. 82: 1726-1730; Clark et al, 1995 Methods in Enzymology 255:395-412; Feig et al, 1998 Molecular and Cellular Biology 8: 3235-3243; Park et al, 2000 Biochemical and Biophysical Research Communications 267: 581-587; Quilliam et al, 1994 Molecular and Cellular Biology 14: 1113-1121).

Briefly, single stock NIH 3T3 cells were propagated in Dulbecco's modified Eagle's medium (Gibco), supplemented with 10% calf serum (Colorado Serum Co., Denver, Colo.), 1% penicillin, 1% streptomycin, 1% L-Glutamine (Gibco), and maintained at 37° in a humidified 10% CO2 incubator. Cells were discarded after 3 passages. Cells were plated in 6 well plates ($2.5 \times 10^5$ cells per well), grown for 24 hours, and then transfected with 0.5 μg of the pcDNA3.1-NS4B plasmid, 0.5 μg pEJ6.6, or both, using Lipofectamine 2000 (Invitrogen). Empty pcDNA3.1 plasmid was co-transfected with pEJ6.6 samples as a source for neomycin-resistance. The total amount of transfected DNA was kept constant at 2 pgs per well by the addition of the empty vector, pUC19, as a carrier. 24 hours following transfection, cells were split at a ratio of 1:20, transferred into 10-cm plates and grown under G418 selection (400 μg/ml) (Invitrogen) for two weeks. G418-18 resistant colonies were stained with crystal violet and colonies larger than 2 mm were counted using ImageJ analysis (NIH) on scanned plates. The experiment was repeated four times, each time with duplicates.

Figure 6:
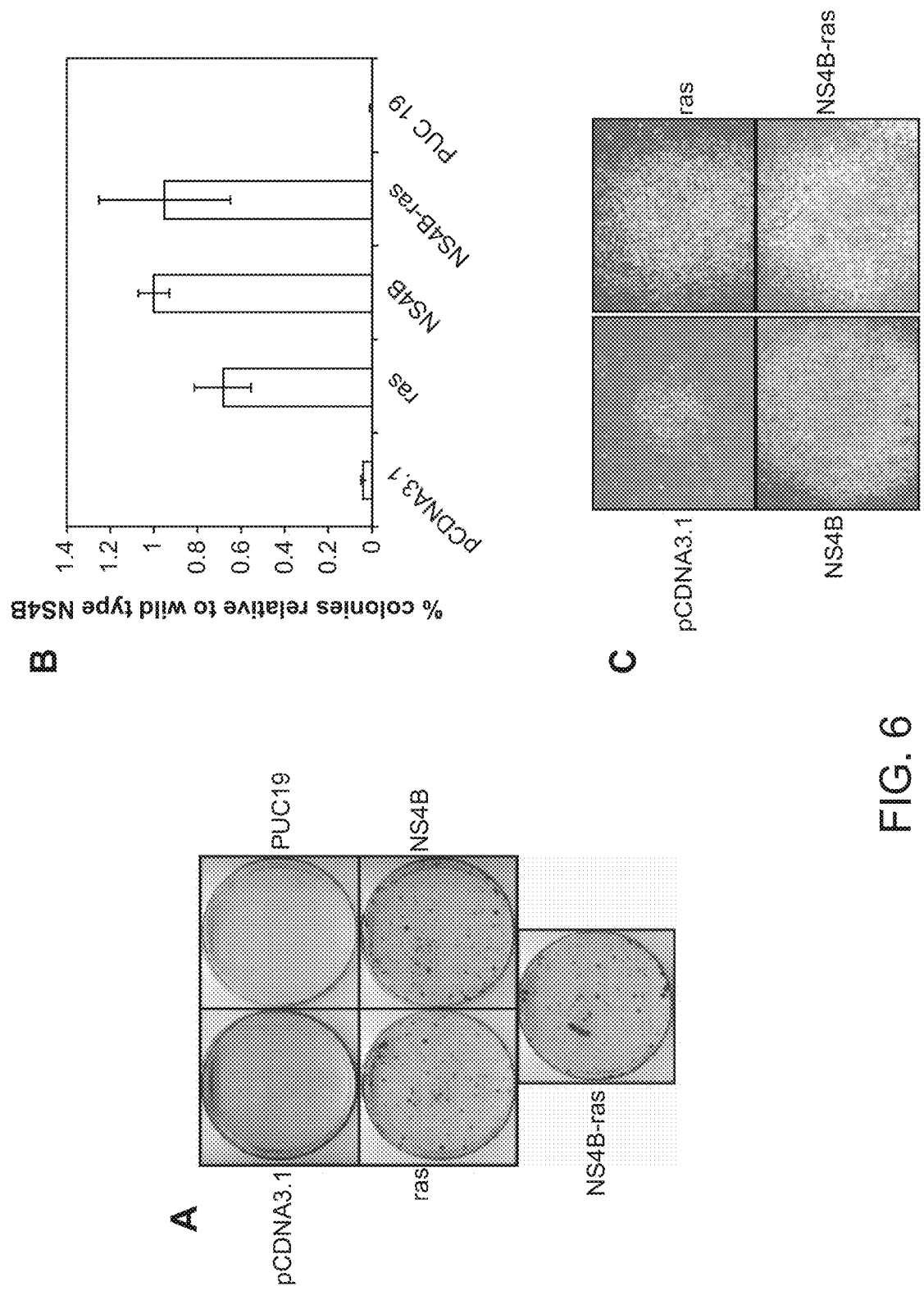
FIG. 6 shows that NS4B of Con1 isolate of genotype 1b transforms NIH 3T3 cells independently of co-transfection with exogenous Ha-ras gene. Panel A: NIH 3T3 cells transfected with empty pcDNA3.1 plasmid encoding neomycin resistance, carrier plasmid pUC19, and plasmids encoding NS4B and/or Ha-ras, were grown under G418 selection for 2 weeks. Representative plates stained with crystal violet are shown. Panel B: Percentages of colonies relative to wild-type (WT) NS4B. Panel C: Morphology of representative colonies assessed by phase-contrast microscopy. Note a multi-layered dense growth characteristic of a loss of density-dependent growth inhibition phenotype in NS4B and ras transfectants but not in empty vector (pcDNA3.1) transfectants.

As shown in FIG. 6, panels A and B, a large number of colonies were detected in cells transfected with NS4B, Ha-ras, or both. Large colonies were present very rarely (<1 per 2 plates) in cells transfected with pcDNA3.1 vector encoding neomycin-resistance only. When present, these were used for background subtraction. As expected, no colonies were seen in cells transfected with just the carrier vector, pUC19. Transfection efficiency was determined using a secreted alkaline phosphatase (SEAP) reporter gene assay (Roche applied science). Relative SEAP activity was measured in the transfected media supernatants using a Berthold LB 96 V luminometer. The transfection efficiency of the various constructs was quite comparable. To exclude the possibility that the observed findings were due to the use of a specific NIH3T3 cell clone, the experiment was repeated using another NIH3T3 cell clone (ATCC). While subtle differences in background did occur, the results described above were not significantly different between the 2 tested clones. Microscopic analysis of the morphology of the G418-resistant colonies (FIG. 6, panel C) revealed a multi-layered dense growth characteristic of a loss of density-dependent growth inhibition phenotype in the NS4B transfectants, similar to that observed in the Ha-ras transfectants. In contrast, pcDNA3.1 transfectants formed monolayers under the same conditions. This suggested that the large colonies detected in the NS4B transfectants were likely transformed. Thus, NS4B indeed transformed NIH3T3 cells when co-expressed with the Ha-ras gene. However, NS4B was able to robustly transform NIH3T3 cells even in the absence of Ha-ras. Furthermore, co-transfection with Ha-ras (pEJ6.6) did not seem to increase the number of transformed foci induced by NS4B alone.

Example 6

Expression of Transfected NS4B and Ha-ras in Stable Cell Lines

Figure 7:
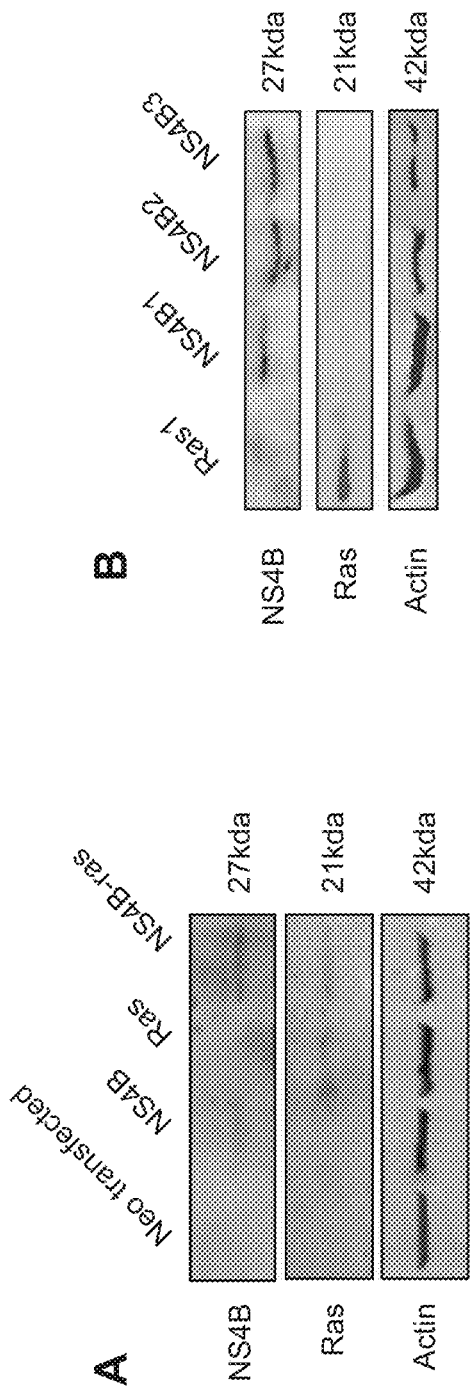
FIG. 7 shows the successful expression of transfected NS4B, Ha-ras or both in transfected cells. Representative colonies were isolated from plates transfected with NS4B, Ha-ras or both, and passaged in the presence of G418. Cell lysates prepared from these stable clones were subjected to western blot analyses using mouse monoclonal anti-NS4B (Virostat), rabbit polyclonal anti-ras (Santa Cruz) and mouse anti-β actin (Sigma) antibodies. Panel A: Expression of NS4B and/or Ha-ras in NS4B, Ha-ras or NS4B-Ha-ras double transfectants. Panel B: Expression of NS4B in various clones of NS4B transfectants.

To determine whether the transfected NS4B and/or Ha-ras were successfully expressed in transfected cells, at least 3 representative colonies from plates transfected with NS4B, Ha-ras or both, and passaged them 3 times in the presence of G418. Cell lysates prepared from these stable clones were then subjected to western blot analyses using mouse anti-NS4B (Virostat) and rabbit anti-ras (Santa Cruz) antibodies. As shown in FIG. 7, Panel A, the appropriate exogenously transfected gene(s) were present. The level of NS4B expression was comparable in the various clones tested (FIG. 7, Panel B). Expression of ras was only detected in cells transfected with activated Ha-ras (FIG. 7, panel A). Although the anti-ras antibody was raised against a domain common to multiple ras isoforms, and in theory should detect endogenous ras proteins as well, only cells transfected with exogenous Ha-ras exhibited detectable level of ras protein. Presumably, this reflects the higher expression level of the transfected isoform, as has been observed by others (Li et al. Journal of Biological Chemistry 279: 37398-37406). Moreover, the expression level of NS4B and ras in NS4B-ras double transfected clones was not lower than their expression level in the NS4B or ras mono-transfected clones (FIG. 7, Panel A). This suggests that the absence of synergy observed between ras and NS4B is not a result of a lower expression level of NS4B or ras in the double transfectants.

Example 7

Transformed Phenotype of NS4B Clones In-Vitro

Figure 8:
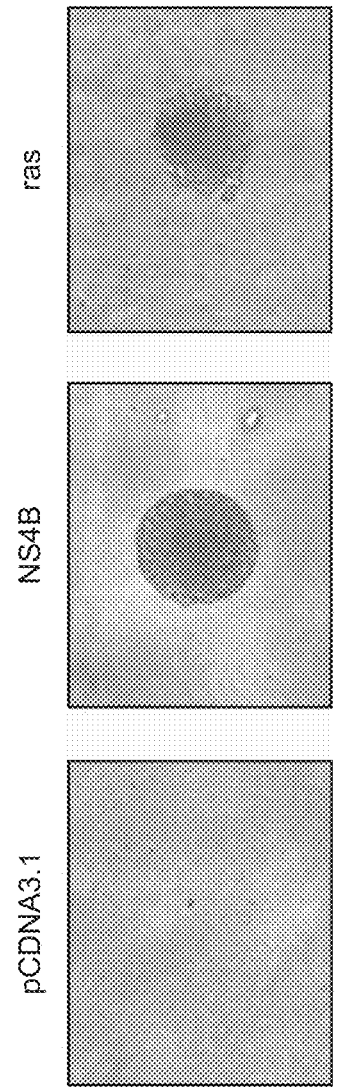
FIG. 8 shows that NS4B clones demonstrate a transformed phenotype in-vitro. Panel A: Transformed phenotype demonstrated by NIH 3T3 cells transfected with WT NS4B. ± indicates standard deviation. Panel B: Anchorage-independent growth: NS4B, ras and empty vector (pcDNA3.1) G418-resistant transfectants were grown in soft agar for 2 weeks. Representative foci are shown.

Confirmation that NS4B-transfected clones are indeed transformed was obtained using several phenotypic in-vitro assays. Standard methods were used to determine the growth rate, saturation density, and serum dependence of the stable clones (Clark et al, 1995 Methods in Enzymology 255:395-412). Briefly, $10^5$ cells were seeded in a 10-cm dish in growth medium and incubated at 37°. Cells were rinsed with PBS, trypsinized and counted daily for seven days. Growth rates were determined from the slope of the logarithmic curve during exponential growth and saturation densities were measured. As shown in FIG. 8, panel A, the doubling time of NS4B clones was 15±2 hours. This was comparable to the doubling time of ras clones (13.7±2.5 hours) and significantly shorter than that of clones established by transfection of empty pcDNA3.1 (32±2.5 hours). Moreover, the saturation density of NS4B clones was ~14 fold higher than that of clones transfected with the empty vector ($10.2\times10^6$ cells vs $0.7\times10^6$) and comparable to that of ras-transformed clones (~$4.5\times10^6$). Furthermore, NS4B and ras clones—but not empty pcDNA3.1 transfectants—continued to readily proliferate in the face of serum depletion (1% FCS) and demonstrated loss of density-dependent growth inhibition when grown to confluence (FIG. 8, panel A).

To determine the anchorage-independent growth potential of the G418-resistant clones, soft agar assays were performed essentially as described in Clark et al, 1995 *Methods in Enzymology* 255:395-412. In brief, cells (5,000 or 20,000 of NS4B, ras and empty pcDNA3.1 stable transfectants) were suspended in 0.25% agar mixture and overlayed onto 0.75% agar in 10 cm dishes. Cells were fed with growth medium weekly. After a 2 week incubation, colony morphology was assessed microscopically and the number of colonies was counted after staining with crystal violet. As shown in FIG. 8, panel B, NS4B-transformed cells were able to form a large number of big foci on soft agar. 153±21 and 467±43 foci formed when 5,000 and 20,000 cells were plated, respectively (FIG. 8, panel A). Similar foci were formed with ras transfectants, however no foci were observed with stable cell lines established from pcDNA3.1-transfected cells (FIG. 8, panel B). While growth in soft agar is not absolutely correlated with tumorigenic potential, this assay is the best in-vitro correlate to in-vivo growth potential (Clark et al, 1995 Methods in Enzymology 255:395-412). These results reveal that NS4B from 1b con-1 isolate can transform NIH 3T3 cells and that these transformed cells demonstrate a classical transformed phenotype.

Example 8

NS4B Clones are Tumorigenic in Nude Mice

To examine whether NS4B transfectants are able to form tumors in-vivo, $10^6$ cells of NS4B stable transfectants were resuspended in 0.1 ml of phosphate buffered saline and injected subcutaneously into the flanks of 4- to 6-week old nude mice (Balb/c nude male, Taconic, Hudson, N.Y.). Five clonal lines of NS4B cells were injected, each into 5 different mice. Three stable clones of ras transfectants were used as a positive control (each injected into 3-5 mice). Non-transfected NIH3T3 cells and neomycin vector alone stably transfected NIH3T3 cells were used as negative controls. Tumor size was measured bi-weekly with linear calipers and cross sectional area was calculated using the formula $3.14\times0.5\times length\times0.5\times width$—shown to correlate best with tumor mass when tumor size is less than 6 gr (Tomayko et al, 1989 Cancer Chemotherapy and Pharmacology 24: 148-154). Tumors were defined as a growth with a section area larger than 1.5 $cm^2$. Mice were sacrificed before tumors reached a cross-sectional area of 2 $cm^2$.

As shown in FIG. 9 (Table 1), two of the NS4B-transfected clones formed tumors with no latency period, appearing within 2 weeks after inoculation. At 2 weeks, one of the positive control Ha-ras-transfected clones similarly formed tumors, while none of the negative control Neo transfectants or non-transfected cells induced tumors. At 5 weeks after inoculation, all but one of the NS4B-transfected clones yielded tumors of considerable size around the inoculation site. Similarly, 2 out of 3 Ras-transfected clones yielded tumors in the same time frame. In contrast, no mice inoculated with Neo alone-transfected cells, and only one (presumably due to spontaneous transformation) of 13 mice inoculated with non-transfected NIH3T3 cells, had developed a tumor after 5 weeks. These data confirm that NS4B has in-vivo tumorigenic potential.

Example 9

NS4B Transformation Potential is Influenced by Genotype Subtype

Figure 10:
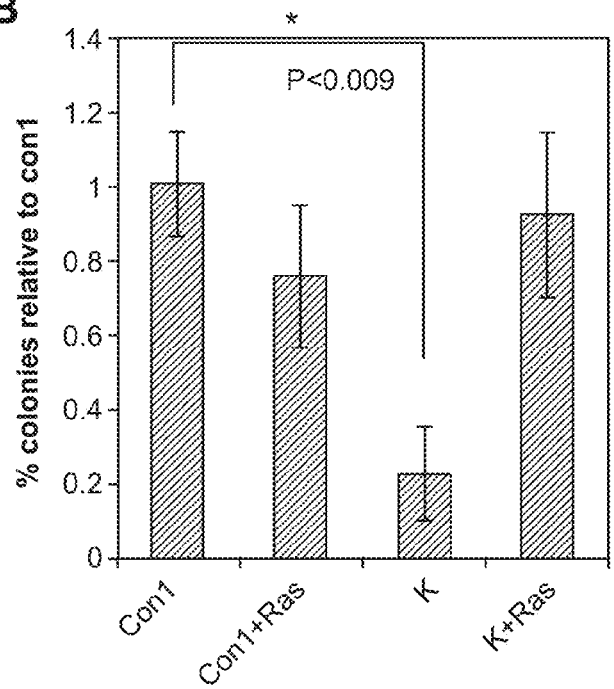
FIG. 10 shows that NS4B transformation potential is influenced by genotype subtype. Panel A: Comparison of the NS4B protein-coding sequences of the Con1 and K isolates. The amino acid sequence of Con1 is shown at the top. ASHLPYIEQGMQLAEQFKQK AIGLLQTATKQAE-AAAPVVESKWRTLEAFWAKHMWNFIS-GIQYLAGLSTLPGNPAIASL MAFTASITSPLTTQHTLL-FNILGGWVAAQLAPPSAASAFVGAGIAGAAVGSIGL-GKVLVD ILAGYGAGVAGALVAFKVMSGEMPST-EDLVNLLPAILSPGALVVGVVCAAILRRHVGP GEGAVQWMNRLIAFASRGNH-VSPTHYVPESDAAARVTQILSS-LTITQLLKRLHQWINED CSTPC: SEQ ID NO: 15. Identical sequences are represented by dashes. Panel B: NS4B of the K isolate was cloned by genetically introducing 7 amino acid changes into the Con1 NS4B. The transformation potential of this construct in the absence of Ha-ras or its presence was tested by the transfection assay in comparison with the Con1 isolate (as in FIG. 6). The asterisk represents a statistically significant difference between the K isolate and the Con1 isolate (p value of 0.0087 in student t-test). Panel C: NS4B K isolate has a similar intracellular distribution pattern to that of the Con1 NS4B isolate. Huh-7 cells plated on coverslips were transfected with plasmids encoding wild-type NS4B-GFP from Con1 or K isolates. 48 hours posttransfection the cells were fixed and imaged by a fluorescence microscope. Panel D: The cellular content of NS4B from the K and Con1 isolates is comparable. Cell lysates were prepared from Con1 or K WT NS4B-GFP and subjected to western blot analysis with rabbit anti-GFP (Molecular probes) and mouse anti-actin (Sigma) antibodies.

In contrast to Park et al, 2000 Biochemical and Biophysical Research Communications 267: 581-587, NS4B did not require co-transfection with Ha-ras in order to achieve NS4B-mediated transformation. Although both of genotype 1b, the NS4B sequence of the con-1 isolate used in the Examples above differs in 7 amino acids from the K isolate used by Park et al. To test the hypothesis that these sequence variations account for the different transforming phenotypes of the two HCV clones, these 7 amino acid changes were introduced by using site directed mutagenesis (using primers 9-18, FIG. 13 (Table 2) and the QuikChange kit (Strategene)) into the Con1 isolate to create an NS4B homologous to the K isolate (FIG. 10, Panel A). The transformation potential of this construct was then tested by the focus formation assay in comparison with the Con1 isolate.

Similarly to Park et al., there was an increase in the number of foci induced by the K isolate with Ha-ras co-transfection. The number of transformed foci induced by the K isolate, however, was significantly (about 5 fold) lower than the number induced by the Con1 NS4B (p value=0.0087 in student t-test) (FIG. 10, Panel B). This was not a result of differences in transfection efficiency, as monitored by SEAP reporter gene assay, or cellular distribution, as assessed by microscopic analysis of GFP fusions of the two NS4B isolates (FIG. 10, Panel C). Nor was there any apparent difference in half-life between the two NS4B isolates, as no difference in the steady-state level of expression of the NS4B-GFP fusions was detected by western blot analysis of transfected Huh7 cells (FIG. 10, Panel D). Again, while co-transfection of activated Ha-ras gene didn't change the number of foci induced by Con1 NS4B, it did increase the number of transformed foci generated by the K isolate by 4 fold, similar to the report by Park et al. Together, these results suggest that the described sequence variations between genotype 1b subtypes account for the difference in activated Ha-ras co-transfection requirement for efficient transformation.

Example 10

The NS4B NBM Mediates Cellular Transformation

Figure 11:
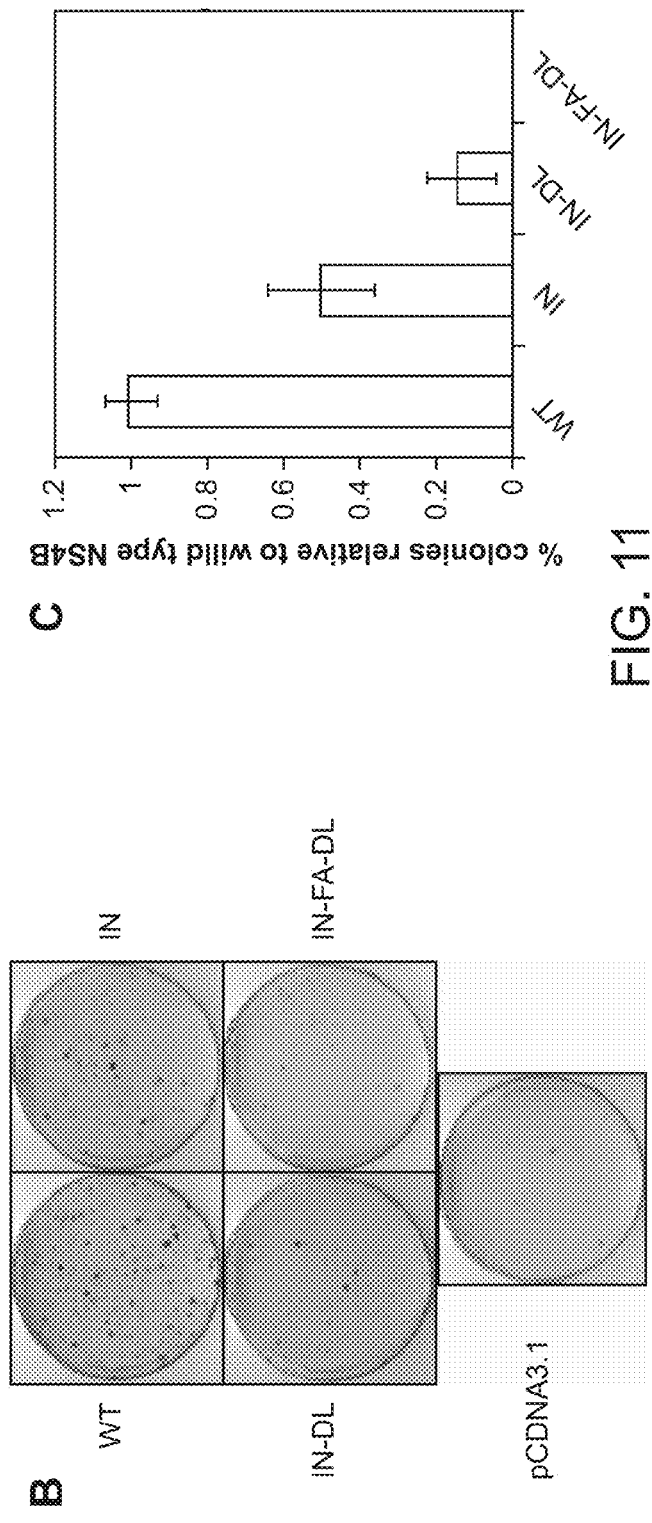
FIG. 11 shows that the NBM of NS4B mediates the latter's role in transformation. Panel A: NBM of HCV NS4B. The amino acid sequence of the consensus of all HCV isolates available for examination (A motif: G(S/G)(I/V)G(L/I)G(K/R): SEQ ID NO: 16, G motif: F, PM2 motif: T, B-Motif DAAA: SEQ ID NO: 17), the genotype 1b clone used in this study (A motif: GSIGLGK: SEQ ID NO: 18, G motif: F, PM2 motif: T, B motif: DAAA: SEQ ID NO:17), and the engineered I131N (A motif: GSNGLGK: SEQ ID NO: 19, G motif: F, PM2 motif T, B motif DAAA: SEQ ID NO:17), I131N-D228L (A motif: GSNGLGK: SEQ ID NO: 19, G motif: F, PM2 motif T, B motif: LAAA: SEQ ID NO:20) and I131N-F211A-D228L (A motif: GSNGLGK: SEQ ID NO: 19, G motif: A, PM2 motif T, B motif LAAA: SEQ ID NO:20) NS4B mutants are indicated. Panel B: NIH 3T3 cells transfected with wild type NS4B or NS4B NBM mutants were grown under G418 selection for 2 weeks. Representative plates stained with crystal violet are shown. Panel C: Percentages of colonies relative to WT NS4B.

To test whether the NBM of NS4B mediates NS4B's role in transformation, the I131IN mutation (IN) was introduced in the A-motif of the NS4B NBM—a mutation previously shown to significantly impair GTPase activity (Einav et al, 2004 J. Virol. 78: 11288-95)—into the pcDNA3.1-NS4B vector by site directed mutagenesis (using primers 3 and 4; FIG. 13 (Table 2) and the QuikChange kit (Stratagene)) (FIG. 11, Panel A). The transformation potential of this mutant was then analyzed by standard transfection assay, as described above. As shown in FIG. 11, Panels B and C, there was a 2 fold reduction in the number of colonies formed in comparison to the WT NS4B construct. While this reduction was found to be statistically significant (p value <0.001 by Student's t test analysis) the IN mutation failed to completely inhibit transformation mediated by NS4B.

Mutations in the NS4B B-(D228L) and G-(F211A) motifs were also introduced by site-directed mutagenesis (using primers 5-8; FIG. 13 (Table 2) and the QuikChange kit (Stratagene)). These combinations of mutations had quite a dramatic effect on NS4B's transforming activity (FIG. 11, Panels B and C). The double mutant containing the IN and DL mutations decreased the number of transformed foci by ~10 fold compared with WT NS4B. Essentially no transformed colonies were formed above the neomycin-transfected background when cells were transfected with the triple mutant harboring point mutations in the A-(IN), B-(DL) and G-(FA) motifs.

These findings were not a result of differences in transfection efficiency (monitored by SEAP reporter gene assay) or simply the result of an obvious gross effect of the mutations on folding, as the apparent intracellular distribution patterns and expression levels of mutant and wild-type GFP-fused proteins appeared similar by fluorescence microscopy and western blotting, respectively (FIG. 12, Panels A and B). These comparable levels of expression suggest that the mutations do not result in any significant difference in half-life between the wild type and mutant versions of NS4B. In addition, representative colonies from the plates transfected with wild type or mutant forms of NS4B were isolated and stable cell lines established. No significant differences in expression levels were noted between WT NS4B and the various mutants, as measured by western blot analysis of cell lysates using a monoclonal mouse anti-NS4B antibody (Virostat) (FIG. 12, Panel C).

Together the above results demonstrate that NS4B can robustly transform NIH3T3 cells in the absence of exogenous Ha-ras. Moreover, the transforming activity of NS4B is mediated by its NBM. Thus, while the data confirm a transforming activity of NS4B described by others (Park et al, 2000 Biochemical and Biophysical Research Communications 267: 581-587), the current results extend their findings and differ in a significant way. Specifically, the results described herein did not show a requirement for co-transfection with Ha-ras in order to achieve Con 1 NS4B-mediated transformation. These findings indicate that this difference in requirement for activate HA-ras co-transfection can be accounted for by the sequence variations between the Con 1 and K genotype 1b isolates.

Interestingly, none of the 7 amino acid mismatches between the K and the Con1 isolate are within the NBM. It is possible that these amino acid mismatches affect NS4B in a way that affects the 3-dimensional conformation of the NBM.

These results reveal that the NBM within NS4B represents an attractive new target for anti-HCC therapy. Because the amino acid sequence immediately adjacent to either side of the NBM region is highly conserved among HCV isolates yet very different from that contained in known host cell GTP-binding proteins, highly selective inhibitors can be readily screened for.

It is evident from the above results and discussion that the assays disclosed herein provide an important new tool for discovery of anti-HCC agents. In particular, the disclosure provides a system for identifying anti-HCC agents based on their ability to inhibit a neoplastic cellular phenotype. As such, the disclosed methods and systems find use in a variety of different applications, including research, medical, therapeutic and other applications.

What is claimed is:

1. A method of screening an agent for activity in modulating a neoplastic cellular phenotype associated with HCV infection, the method comprising:
    (i) contacting a candidate agent with a mammalian expressing a full length hepatitis C virus (HCV) NS4B polypeptide,
    wherein the amino acid sequences of the A motif, G motif, PM2 motif and B motif of the nucleotide binding motif (NBM) of the NS4B polypeptide are G(S/G)(I/V/N)G (LI)G(K/R) of SEQ ID NO:16 or 18, phenylalanine (F), threonine (T), and (D/L)AAA of SEQ ID NO:17 or 20, respectively,
    wherein the NS4B NBM polypeptide can bind a nucleotide, and wherein expression of the NS4B NBM polypeptide in the absence of candidate agent promotes a neoplastic cellular phenotype of the cell, with the proviso that the mammalian cell does not express an exogenous Ha-ras oncogene; and
    (ii) detecting the presence or absence of an effect of said candidate agent on the neoplastic cellular phenotype mediated by the NS4B-NBM polypeptide, wherein said detecting indicates the activity of the candidate agent in modulating NS4B-mediated promotion of a neoplastic cellular phenotype.

2. The method of claim 1, wherein the mammalian cell expressing said functional viral NS4B polypeptide is an NIH3T3 cell.

3. The method of claim 1, wherein the neoplastic cellular phenotype is abnormal cell growth in an immuno-compromised non-human animal model.

4. The method of claim 1, wherein said functional viral NS4B NBM polypeptide is a Con1 NS4B isolate.

5. The method of claim 1, wherein the amino acid sequence of said functional viral NS4B NBM polypeptide is SEQ ID NO:15.

6. The method of claim 1, wherein the neoplastic cellular phenotype is abnormal cellular proliferation.

7. The method of claim 1, wherein the neoplastic cellular phenotype is loss of density dependent growth inhibition.

8. The method of claim 1, wherein the neoplastic cellular phenotype is continued cellular proliferation despite serum depletion.

9. The method of claim 1, wherein the neoplastic cellular phenotype is anchorage-independent growth potential.

10. The method of claim 1, wherein the neoplastic cellular phenotype is an ability to promote tumor growth and/or development in an immuno-compromised non-human animal model.

11. The method of claim 5, wherein the amino acid sequence of said functional viral NS4B NBM polypeptide is SEQ ID NO: 15 except for one or two amino acid substitutions selected from the group consisting of I131N, K135S, K135R, and F211A.

12. The method of claim 11, wherein the amino acid sequence of said functional viral NS4B NBM polypeptide is SEQ ID NO: 15 except for a substitution of I131N.

13. The method of claim 11, wherein the amino acid sequence of said functional viral NS4B NBM polypeptide is SEQ ID NO: 15 except for substitutions of I131N and F211A.

14. The method of claim 11, wherein the amino acid sequence of said functional viral NS4B NBM polypeptide is SEQ ID NO: 15 except for substitutions of F211A and D228L.

15. The method of claim 11, wherein the amino acid sequence of said functional viral NS4B NBM polypeptide is SEQ ID NO: 15 except for a substitution of K135S.

16. The method of claim 11, wherein the amino acid sequence of said functional viral NS4B NBM polypeptide is SEQ ID NO: 15 except for a substitution of K135R.

17. The method of claim 1, comprising determining the effect of the candidate agent on a nucleotide binding activity, a nucleotide hydrolyzing activity, or a nucleotide-dependent RNA binding activity of the NS4B-NSM polypeptide.

18. A method of screening an agent for activity in modulating a neoplastic cellular phenotype, the method comprising:
    contacting a candidate agent with a mammalian cell expressing a functional full length viral NS4B nucleotide binding motif (NBM) polypeptide of a hepatitis C virus (HCV), wherein the NS4B NBM polypeptide comprises the amino acid sequence of SEQ ID NO:15 except for one or more amino acid substitutions at positions corresponding to residues selected from the group consisting of residue 131, 135, 211, and 228, wherein the NS4B NBM polypeptide can bind a nucleotide, and wherein expression of the NS4B NBM polypeptide in the absence of candidate agent promotes a neoplastic cellular phenotype of the cell, with the proviso that the mammalian cell does not express an exogenous Ha-ras oncogene; and
    detecting the presence or absence of an effect of said candidate agent on the neoplastic cellular phenotype mediated by the NS4B-NBM polypeptide;
    wherein said detecting indicates the activity of the candidate agent in modulating NS4B-mediated promotion of a neoplastic cellular phenotype.

\* \* \* \* \*

SEQUENCE LISTING

```
<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: (2)...(5)
<223> OTHER INFORMATION: Xaa = Any Amino Acid
<220> FEATURE:
<221> NAME/KEY: VARIANT
<222> LOCATION: 8
```

```
<223> OTHER INFORMATION: Xaa = S or T

<400> SEQUENCE: 1

Gly Xaa Xaa Xaa Xaa Gly Lys Xaa
 1               5

<210> SEQ ID NO 2
<211> LENGTH: 8
<212> TYPE: PRT
<213> ORGANISM: Homo sapiens
<220> FEATURE:
<221> NAME/KEY: VARIANT
<222> LOCATION: 2
<223> OTHER INFORMATION: Xaa = Any Amino Acid

<400> SEQUENCE: 2

Gly Xaa Gly Gly Val Gly Lys Ser
 1               5

<210> SEQ ID NO 3
<211> LENGTH: 8
<212> TYPE: PRT
<213> ORGANISM: Homo sapiens
<220> FEATURE:
<221> NAME/KEY: VARIANT
<222> LOCATION: 5
<223> OTHER INFORMATION: Xaa = any amino acid

<400> SEQUENCE: 3

Gly Asp Gly Ala Xaa Gly Lys Thr
 1               5

<210> SEQ ID NO 4
<211> LENGTH: 8
<212> TYPE: PRT
<213> ORGANISM: Homo sapiens

<400> SEQUENCE: 4

Gly Leu Asp Ala Ala Gly Lys Thr
 1               5

<210> SEQ ID NO 5
<211> LENGTH: 8
<212> TYPE: PRT
<213> ORGANISM: Homo sapiens

<400> SEQUENCE: 5

Gly His Val Asp His Gly Lys Thr
 1               5

<210> SEQ ID NO 6
<211> LENGTH: 4
<212> TYPE: PRT
<213> ORGANISM: Homo sapiens

<400> SEQUENCE: 6

Asp Thr Ala Gly
 1

<210> SEQ ID NO 7
<211> LENGTH: 4
<212> TYPE: PRT
<213> ORGANISM: Homo sapiens

<400> SEQUENCE: 7

Asp Val Gly Gly
```

```
<210> SEQ ID NO 8
<211> LENGTH: 4
<212> TYPE: PRT
<213> ORGANISM: Homo sapiens

<400> SEQUENCE: 8

Asp Cys Pro Gly
 1

<210> SEQ ID NO 9
<211> LENGTH: 8
<212> TYPE: PRT
<213> ORGANISM: P4 Phage

<400> SEQUENCE: 9

Gly Pro Gly Gly Ser Gly Lys Ser
 1               5

<210> SEQ ID NO 10
<211> LENGTH: 8
<212> TYPE: PRT
<213> ORGANISM: Hepatitis A virus

<400> SEQUENCE: 10

Gly Lys Arg Gly Gly Gly Lys Ser
 1               5

<210> SEQ ID NO 11
<211> LENGTH: 8
<212> TYPE: PRT
<213> ORGANISM: Polio virus

<400> SEQUENCE: 11

Gly Ser Pro Gly Thr Gly Lys Ser
 1               5

<210> SEQ ID NO 12
<211> LENGTH: 8
<212> TYPE: PRT
<213> ORGANISM: Bovine parvovirus

<400> SEQUENCE: 12

Gly Pro Ala Ser Thr Gly Lys Thr
 1               5

<210> SEQ ID NO 13
<211> LENGTH: 8
<212> TYPE: PRT
<213> ORGANISM: Cowpea mosaic virus

<400> SEQUENCE: 13

Gly Lys Ser Arg Thr Gly Lys Ser
 1               5

<210> SEQ ID NO 14
<211> LENGTH: 8
<212> TYPE: PRT
<213> ORGANISM: Rabbit haemorrhagic disease virus

<400> SEQUENCE: 14

Gly Ala Pro Gly Ile Gly Lys Thr
 1               5
```

```
<210> SEQ ID NO 15
<211> LENGTH: 261
<212> TYPE: PRT
<213> ORGANISM: Hepatitis C virus

<400> SEQUENCE: 15

Ala Ser His Leu Pro Tyr Ile Glu Gln Gly Met Gln Leu Ala Glu Gln
 1               5                  10                  15

Phe Lys Gln Lys Ala Ile Gly Leu Leu Gln Thr Ala Thr Lys Gln Ala
            20                  25                  30

Glu Ala Ala Pro Val Val Glu Ser Lys Trp Arg Thr Leu Glu Ala
        35                  40                  45

Phe Trp Ala Lys His Met Trp Asn Phe Ile Ser Gly Ile Gln Tyr Leu
50                  55                  60

Ala Gly Leu Ser Thr Leu Pro Gly Asn Pro Ala Ile Ala Ser Leu Met
65                  70                  75                  80

Ala Phe Thr Ala Ser Ile Thr Ser Pro Leu Thr Thr Gln His Thr Leu
                85                  90                  95

Leu Phe Asn Ile Leu Gly Gly Trp Val Ala Ala Gln Leu Ala Pro Pro
            100                 105                 110

Ser Ala Ala Ser Ala Phe Val Gly Ala Gly Ile Ala Gly Ala Ala Val
        115                 120                 125

Gly Ser Ile Gly Leu Gly Lys Val Leu Val Asp Ile Leu Ala Gly Tyr
130                 135                 140

Gly Ala Gly Val Ala Gly Ala Leu Val Ala Phe Lys Val Met Ser Gly
145                 150                 155                 160

Glu Met Pro Ser Thr Glu Asp Leu Val Asn Leu Leu Pro Ala Ile Leu
                165                 170                 175

Ser Pro Gly Ala Leu Val Val Gly Val Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
210                 215                 220

Pro Glu Ser Asp Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260

<210> SEQ ID NO 16
<211> LENGTH: 7
<212> TYPE: PRT
<213> ORGANISM: Artificial Sequence
<220> FEATURE:
<223> OTHER INFORMATION: A Motif Consensus Sequence
<220> FEATURE:
<221> NAME/KEY: VARIANT
<222> LOCATION: 2
<223> OTHER INFORMATION: Xaa = S or G
<220> FEATURE:
<221> NAME/KEY: VARIANT
<222> LOCATION: 3
<223> OTHER INFORMATION: Xaa = I or V
<220> FEATURE:
<221> NAME/KEY: VARIANT
<222> LOCATION: 5
<223> OTHER INFORMATION: Xaa = L or I
<220> FEATURE:
```

```
<221> NAME/KEY: VARIANT
<222> LOCATION: 7
<223> OTHER INFORMATION: Xaa = K or R

<400> SEQUENCE: 16

Gly Xaa Xaa Gly Xaa Gly Xaa
 1               5

<210> SEQ ID NO 17
<211> LENGTH: 4
<212> TYPE: PRT
<213> ORGANISM: Artificial Sequence
<220> FEATURE:
<223> OTHER INFORMATION: B Motif Consensus Sequence

<400> SEQUENCE: 17

Asp Ala Ala Ala
 1

<210> SEQ ID NO 18
<211> LENGTH: 7
<212> TYPE: PRT
<213> ORGANISM: Hepatitis C Virus

<400> SEQUENCE: 18

Gly Ser Ile Gly Leu Gly Lys
 1               5

<210> SEQ ID NO 19
<211> LENGTH: 7
<212> TYPE: PRT
<213> ORGANISM: Hepatitis C Virus Mutant

<400> SEQUENCE: 19

Gly Ser Asn Gly Leu Gly Lys
 1               5

<210> SEQ ID NO 20
<211> LENGTH: 4
<212> TYPE: PRT
<213> ORGANISM: Hepatitis C Virus Mutant

<400> SEQUENCE: 20

Leu Ala Ala Ala
 1

<210> SEQ ID NO 21
<211> LENGTH: 44
<212> TYPE: PRT
<213> ORGANISM: Artificial Sequence
<220> FEATURE:
<223> OTHER INFORMATION: Primer

<400> SEQUENCE: 21

Cys Gly Cys Gly Gly Ala Thr Cys Cys Gly Gly Ala Thr Gly Gly
 1               5                  10                  15

Cys Cys Thr Cys Ala Cys Ala Cys Cys Thr Cys Cys Cys Thr Thr Ala
            20                  25                  30

Cys Ala Thr Cys Gly Ala Ala Cys Ala Gly Gly Gly
                35                  40

<210> SEQ ID NO 22
<211> LENGTH: 34
<212> TYPE: PRT
<213> ORGANISM: Artificial Sequence
```

<220> FEATURE:
<223> OTHER INFORMATION: Primer

<400> SEQUENCE: 22

Cys Cys Gly Gly Ala Ala Thr Thr Cys Cys Thr Ala Gly Cys Ala Thr
1               5                   10                  15

Gly Gly Cys Gly Thr Gly Gly Ala Gly Cys Ala Gly Thr Cys Cys Thr
            20                  25                  30

Cys Gly

<210> SEQ ID NO 23
<211> LENGTH: 34
<212> TYPE: PRT
<213> ORGANISM: Artificial Sequence
<220> FEATURE:
<223> OTHER INFORMATION: Primer

<400> SEQUENCE: 23

Gly Cys Gly Gly Cys Thr Gly Thr Thr Gly Gly Cys Ala Gly Cys Ala
1               5                   10                  15

Ala Cys Gly Gly Cys Cys Thr Thr Gly Gly Ala Ala Gly Gly Thr
            20                  25                  30

Gly Cys

<210> SEQ ID NO 24
<211> LENGTH: 34
<212> TYPE: PRT
<213> ORGANISM: Artificial Sequence
<220> FEATURE:
<223> OTHER INFORMATION: Primer

<400> SEQUENCE: 24

Gly Cys Ala Cys Cys Thr Thr Cys Cys Cys Ala Ala Gly Gly Cys Cys
1               5                   10                  15

Gly Thr Thr Gly Cys Thr Gly Cys Cys Ala Ala Cys Ala Gly Cys Cys
            20                  25                  30

Gly Cys

<210> SEQ ID NO 25
<211> LENGTH: 40
<212> TYPE: PRT
<213> ORGANISM: Artificial Sequence
<220> FEATURE:
<223> OTHER INFORMATION: Primer

<400> SEQUENCE: 25

Gly Thr Gly Cys Cys Thr Gly Ala Gly Ala Gly Cys Cys Thr Cys Gly
1               5                   10                  15

Cys Thr Gly Cys Ala Gly Cys Ala Cys Gly Thr Gly Thr Cys Ala Cys
            20                  25                  30

Thr Cys Ala Gly Ala Thr Cys Cys
        35                  40

<210> SEQ ID NO 26
<211> LENGTH: 40
<212> TYPE: PRT
<213> ORGANISM: Artificial Sequence
<220> FEATURE:
<223> OTHER INFORMATION: Primer

<400> SEQUENCE: 26

Gly Thr Gly Cys Cys Thr Gly Ala Gly Ala Gly Cys Cys Thr Cys Gly

```
                1               5                   10                  15
Cys Thr Gly Cys Ala Gly Cys Ala Cys Gly Thr Gly Thr Cys Ala Cys
                20                  25                  30

Thr Cys Ala Gly Ala Thr Cys Cys
        35                  40

<210> SEQ ID NO 27
<211> LENGTH: 39
<212> TYPE: PRT
<213> ORGANISM: Artificial Sequence
<220> FEATURE:
<223> OTHER INFORMATION: Primer

<400> SEQUENCE: 27

Gly Gly Ala Thr Gly Ala Ala Cys Cys Gly Gly Cys Thr Gly Ala Thr
1               5                   10                  15

Ala Gly Cys Gly Gly Cys Cys Gly Cys Thr Thr Cys Gly Cys Gly Gly
                20                  25                  30

Gly Gly Thr Ala Ala Cys Cys
        35

<210> SEQ ID NO 28
<211> LENGTH: 38
<212> TYPE: PRT
<213> ORGANISM: Artificial Sequence
<220> FEATURE:
<223> OTHER INFORMATION: Primer

<400> SEQUENCE: 28

Gly Gly Thr Thr Ala Cys Cys Cys Gly Cys Gly Ala Ala Gly Cys
1               5                   10                  15

Gly Gly Cys Cys Gly Cys Thr Ala Thr Cys Ala Gly Cys Cys Gly Gly
                20                  25                  30

Thr Thr Cys Ala Thr Cys
        35

<210> SEQ ID NO 29
<211> LENGTH: 29
<212> TYPE: PRT
<213> ORGANISM: Artificial Sequence
<220> FEATURE:
<223> OTHER INFORMATION: Primer

<400> SEQUENCE: 29

Cys Ala Thr Cys Gly Ala Ala Cys Ala Gly Gly Gly Ala Gly Thr Gly
1               5                   10                  15

Cys Ala Gly Cys Thr Cys Gly Cys Cys Gly Ala Ala Cys
                20                  25

<210> SEQ ID NO 30
<211> LENGTH: 29
<212> TYPE: PRT
<213> ORGANISM: Artificial Sequence
<220> FEATURE:
<223> OTHER INFORMATION: Primer

<400> SEQUENCE: 30

Gly Thr Thr Cys Gly Gly Cys Gly Ala Gly Cys Thr Gly Cys Ala Cys
1               5                   10                  15

Thr Cys Cys Cys Thr Gly Thr Thr Cys Gly Ala Thr Gly
                20                  25
```

```
<210> SEQ ID NO 31
<211> LENGTH: 33
<212> TYPE: PRT
<213> ORGANISM: Artificial Sequence
<220> FEATURE:
<223> OTHER INFORMATION: Primer

<400> SEQUENCE: 31

Cys Ala Ala Cys Ala Gly Ala Ala Gly Gly Cys Ala Cys Thr Cys
1               5                   10                  15

Gly Gly Gly Thr Thr Gly Cys Thr Gly Cys Ala Ala Cys Ala Gly
            20                  25                  30

Cys

<210> SEQ ID NO 32
<211> LENGTH: 33
<212> TYPE: PRT
<213> ORGANISM: Artificial Sequence
<220> FEATURE:
<223> OTHER INFORMATION: Primer

<400> SEQUENCE: 32

Gly Cys Thr Gly Thr Thr Thr Gly Cys Ala Gly Cys Ala Ala Cys Cys
1               5                   10                  15

Cys Gly Ala Gly Thr Gly Cys Cys Thr Thr Cys Thr Gly Thr Thr Thr
            20                  25                  30

Gly

<210> SEQ ID NO 33
<211> LENGTH: 36
<212> TYPE: PRT
<213> ORGANISM: Artificial Sequence
<220> FEATURE:
<223> OTHER INFORMATION: Primer

<400> SEQUENCE: 33

Cys Cys Ala Ala Gly Thr Gly Gly Cys Gly Gly Cys Cys Cys Thr
1               5                   10                  15

Cys Gly Ala Ala Cys Cys Cys Thr Thr Cys Thr Gly Gly Gly Cys Gly
            20                  25                  30

Ala Ala Gly Cys
        35

<210> SEQ ID NO 34
<211> LENGTH: 36
<212> TYPE: PRT
<213> ORGANISM: Artificial Sequence
<220> FEATURE:
<223> OTHER INFORMATION: Primer

<400> SEQUENCE: 34

Gly Cys Thr Thr Cys Gly Cys Cys Cys Ala Gly Ala Ala Gly Gly Gly
1               5                   10                  15

Thr Thr Cys Gly Ala Gly Gly Gly Cys Cys Gly Cys Cys Ala Cys
            20                  25                  30

Thr Thr Gly Gly
        35

<210> SEQ ID NO 35
<211> LENGTH: 31
<212> TYPE: PRT
<213> ORGANISM: Artificial Sequence
<220> FEATURE:
```

<223> OTHER INFORMATION: Primer

<400> SEQUENCE: 35

Gly Cys Thr Cys Ala Cys Cys Ala Cys Cys Ala Ala Ala Thr
1               5                   10                  15
Ala Cys Cys Cys Thr Cys Cys Thr Gly Thr Thr Ala Ala Cys
                20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Primer

<400> SEQUENCE: 36

Gly Thr Thr Ala Ala Ala Cys Ala Gly Gly Ala Gly Gly Thr Ala
1               5                   10                  15
Thr Thr Thr Thr Gly Gly Gly Thr Gly Gly Thr Gly Ala Gly Cys
                20                  25                  30

<210> SEQ ID NO 37
<211> LENGTH: 38
<212> TYPE: PRT
<213> ORGANISM: Artificial Sequence
<220> FEATURE:
<223> OTHER INFORMATION: Primer

<400> SEQUENCE: 37

Gly Gly Cys Cys Thr Thr Thr Ala Ala Gly Ala Thr Cys Ala Thr Gly
1               5                   10                  15
Ala Gly Cys Gly Gly Cys Gly Ala Gly Gly Thr Gly Cys Cys Cys Thr
                20                  25                  30
Cys Cys Ala Cys Cys Gly
        35

<210> SEQ ID NO 38
<211> LENGTH: 38
<212> TYPE: PRT
<213> ORGANISM: Artificial Sequence
<220> FEATURE:
<223> OTHER INFORMATION: Primer

<400> SEQUENCE: 38

Cys Gly Gly Thr Gly Gly Ala Gly Gly Gly Cys Ala Cys Cys Thr Cys
1               5                   10                  15
Gly Cys Cys Gly Cys Thr Cys Ala Thr Gly Ala Thr Cys Thr Thr Ala
                20                  25                  30
Ala Ala Gly Gly Cys Cys
        35

<210> SEQ ID NO 39
<211> LENGTH: 7
<212> TYPE: PRT
<213> ORGANISM: Artificial Sequence
<220> FEATURE:
<223> OTHER INFORMATION: A Motif Consensus Sequence
<220> FEATURE:
<221> NAME/KEY: VARIANT
<222> LOCATION: 2
<223> OTHER INFORMATION: Xaa = Ser or Gly
<220> FEATURE:
<221> NAME/KEY: VARIANT
<222> LOCATION: 7
<223> OTHER INFORMATION: Xaa = Lys or Arg

```
<400> SEQUENCE: 39

Gly Xaa Ile Gly Leu Gly Xaa
 1               5
```